US012686885B2

(12) United States Patent (10) Patent No.: US 12,686,885 B2
Satterly et al. (45) Date of Patent: Jul. 21, 2026

(54) DEVICES AND METHODS FOR NUCLEIC ACID IDENTIFICATION IN SAMPLES

(71) Applicant: Chemring Sensors and Electronic Systems, Inc., Dulles, VA (US)

(72) Inventors: Neal G. Satterly, Tega Cay, SC (US); Kevin P. Pfeuffer, Charlotte, NC (US)

(73) Assignee: CHEMRING SENSORS AND ELECTRONIC SYSTEMS, INC., Dulles, VA (US)

( * ) Notice: Subject to any disclaimer, the term of this patent is extended or adjusted under 35 U.S.C. 154(b) by 904 days.

(21) Appl. No.: 17/710,044

(22) Filed: Mar. 31, 2022

(65) Prior Publication Data

US 2022/0315993 A1 Oct. 6, 2022

Related U.S. Application Data

(60) Provisional application No. 63/200,884, filed on Apr. 1, 2021.

(51) Int. Cl.
| | |
|---|---|
| *C12Q 1/6816* | (2018.01) |
| *B01L 7/00* | (2006.01) |
| *C12Q 1/686* | (2018.01) |
| *C12Q 1/6876* | (2018.01) |

(52) U.S. Cl.
CPC .............. *C12Q 1/6816* (2013.01); *B01L 7/52* (2013.01); *C12Q 1/686* (2013.01); *C12Q 1/6876* (2013.01); *C12Q 2563/107* (2013.01)

(58) Field of Classification Search
CPC ............ C12Q 2531/125; C12Q 1/6844; C12Q 2565/629; B01L 2400/0427
See application file for complete search history.

(56) References Cited

U.S. PATENT DOCUMENTS

| | | | |
|---|---|---|---|
| 8,557,199 | B2 | 10/2013 | Heath et al. |
| 9,579,655 | B2 | 2/2017 | DeJohn et al. |
| 10,209,246 | B2 | 2/2019 | Debski et al. |
| 10,745,745 | B2 | 8/2020 | Belhocine et al. |
| 10,822,640 | B2 | 11/2020 | Dahl et al. |
| 2015/0252351 | A1 | 9/2015 | McGall et al. |
| 2017/0322136 | A1 | 11/2017 | Garstecki et al. |
| 2018/0282792 | A1 | 10/2018 | Ito et al. |
| 2019/0344280 | A1 | 11/2019 | Pasko et al. |
| 2020/0399687 | A1 | 12/2020 | Frisen et al. |

FOREIGN PATENT DOCUMENTS

| | | | | |
|---|---|---|---|---|
| JP | 2006-527597 | A | 12/2006 | |
| JP | 2014-506465 | A | 3/2014 | |
| WO | WO-2012109500 | A2 * | 8/2012 | ............ C12N 15/10 |
| WO | 2017158840 | A1 | 9/2017 | |
| WO | 2017223026 | A1 | 12/2017 | |
| WO | 2018053174 | A1 | 3/2018 | |
| WO | 2020132005 | A1 | 6/2020 | |

OTHER PUBLICATIONS

Marciniak et al., "Coupled Rolling Circle Amplification Loop-Mediated Amplification for Rapid Detection of Short DNA Sequences," Biotechniques, vol. 45, pp. 275-280. (Year: 2008).*
Lou et al., "High-throughput DNA sequencing errors are reduced by orders of magnitude using circle sequencing," PNAS, vol. 110, No. 49, pp. 19872-19877. (Year: 2013).*
Tanner et al., "Simultaneous multiple target detection in real-time loop-mediated isothermal amplification," BioTechniques, vol. 53, pp. 81-89. (Year: 2012).*
Gudnason H. et al. "Comparison of multiple DNA dyes for real-time PCR: effect of dye concentration and sequence composition on DNA amplification and melting temperature" Nucleic Acids Research (Sep. 26, 2007; vol. 35; No. 19; e127) (8 pages total).
Marciniak J.Y. et al. "Coupled rolling circle amplification loop-mediated amplification for rapid detection of short DNA sequences" BioTechniques (Sep. 2008; vol. 45; No. 3) pp. 275-280.
Kuhnemund M. et al. "Circle-to-circle amplification on a digital microfluidic chip for amplified single molecule detection" Lab Chip (Jun. 5, 2014; vol. 14) pp. 2983-2992.
Kalsi S. et al. "Rapid and sensitive detection of antibiotic resistance on a programmable digital microfluidic platform" Lab Chip 15 (Jun. 18, 2015; vol. 15) pp. 3065-3075.
Oscorbin P. et al. "Comparison of fluorescent intercalating dyes for quantitative loop-mediated isothermal amplification (qLAMP)" BioTechniques (Jul. 1, 2016; vol. 61; No. 1) pp. 20-25 (10 pages total).
Coelho B. et al. "Digital Microfluidics for Nucleic Acid Amplification" Sensors (Jun. 25, 2017; vol. 17; 1495) (13 pages total).
Wan L. et al. "A digital microfluidic system for loop-mediated isothermal amplification and sequence specific pathogen detection" Sci. Rep. (Nov. 6, 2017; vol. 7; 14586) (11 pages total).
Coelho B. et al. "A digital microfluidics platform for loop-mediated isothermal amplification detection" Sensors (Nov. 16, 2017; vol. 17; 2616) (11 pages total).

(Continued)

*Primary Examiner* — Young J Kim
(74) *Attorney, Agent, or Firm* — Boyle PLLC, Patent & Technology Law

(57) ABSTRACT

A device, method, and non-transitory computer readable medium storing instructions for nucleic acid identification of material in a sample includes a microfluidics system, including a movable cartridge, and a heat source. The movable cartridge assembly includes at least one target-specific set of reagent components and a set of RCA-LAMP reaction components deposited on the surface. Moreover, the at least one target-specific set of reagent components includes at least one target specific padlock probe reagent component. The set of RCA-LAMP reaction components includes: at least one polymerase buffer component, at least one polymerase enzyme with strand displacement activity, a betaine additive, a TETRONIC additive, a sequence-specific probe, dNTPs, and a primer mix. The primer mix includes both a forward inside primer and a backward inside primer specific to a backbone of the at least one target specific padlock probe reagent component.

20 Claims, 31 Drawing Sheets

(56) References Cited

OTHER PUBLICATIONS

Neumann F. et al. "Padlock Probe Assay for Detection and Subtyping of Seasonal Influenza" Clinical Chemistry (Dec. 1, 2018; vol. 64; No. 12) pp. 1704-1712.

Tian W. et al. "Rolling Circle extension-actuated loop-mediated isothermal amplification (RCA-LAMP) for ultrasensitive detection of microRNAs" Biosensors and Bioelectronics (Dec. 7, 2018; vol. 128) pp. 17-22.

Wan L. et al. "LampPort: a handheld digital microfluidic device for loop-mediated isothermal amplification (LAMP)" Biomed Microdevices (Jan. 7, 2019; vol. 21) (8 pages total).

Zhang K. et al. "Rolling Circle Amplification as an Efficient Analytical Tool for Rapid Detection of Contaminants in Aqueous Environments" Biosensors (Sep. 23, 2021; vol. 11; 352) (30 pages total).

Cao Z. et al. "Rolling Circle and Loop Mediated Isothermal Amplification Strategy for Ultrasensitive miRNA Detection" Separations (Oct. 3, 2021; vol. 8; 166) (11 pages total).

Zhang B. et al. "Anti-Interference Detection of Vibrio parahaemolyticus from Aquatic Food Based on Target-Cyclized RCA with Dynamic Adapter Followed by LAMP" Foods (Jan. 26, 2022; 11; 352) (13 pages total).

International Search Report for corresponding International Application PCT/US2022/022781 (Mailing date: Jul. 25, 2022) (6 pages total).

Written Opinion of the International Search Authority for corresponding International Application PCT/US2022/022781 (Mailing date: Jul. 25, 2022) (7 pages total).

Kim, T. et al. "Recent Advances of Fluid Manipulation Technologies in Microfluidic Paper-Based Analytical Devices ([mu]PADs) toward Multi-Step Assays" Micromachines 2020 (Mar. 4, 2020; vol. 11, No. 3) p. 269 (30 pages total).

Troger, V. et al. "Isothermal Amplification and Quantification of Nucleic Acids and its Use in Microsystems," Journal of Nanomedicine & Nanotechnology 2015 ( vol. 6, Iss. 3, 1000282) (20 pages total.).

Ciftci, S. "Padlock Probe-Based Nucleic Acid Amplification Tests: Point-of-care Diagnostics of Infectious Diseases" (Doctoral Thesis in Biochemistry at Stockholm University, Sweden, 2019) (Publicly Defended: May 15, 2019) (81 pages total).

Office Action mailed Mar. 10, 2026, in related Japanese Patent Appl. No. 2023-560978 (including English language translation) (10 pages total).

* cited by examiner

DEVICES AND METHODS FOR NUCLEIC ACID IDENTIFICATION IN SAMPLES

CROSS REFERENCE TO RELATED APPLICATIONS

This application claims the priority and benefit of U.S. Provisional Application No. 63/200,884, filed on Apr. 1, 2021, which is hereby incorporated by reference in its entirety.

TECHNICAL FIELD

This disclosure relates to devices, methods, and non-transitory computer readable media storing instructions for the amplification and identification of genetic materials that may be present in samples.

BACKGROUND

One of the primary methods used to identify the presence of an organism is the mass amplification of some or all of its genetic material. When originally developed, amplification reactions relied on thermocycling (repeated heating and cooling) certain polymerases to amplify a target organism's genetic material (i.e., polymerase chain reaction, "PCR"). Thermocycling requires dedicated laboratory equipment and a unique primer set for each target to be detected. It is also relatively slow and expensive.

Since the development of thermocycling amplification, efforts have been made to increase the speed and sensitivity of genetic material amplification, reduce its cost, and make it easier to perform. Rolling circle amplification ("RCA") using padlock probes is one of those reactions. It has been used for nearly thirty years and is advantageous because it is an isothermal method (i.e., does not require thermocycling) that can detect the genetic material of specific organisms. Also, it does not require as much assay development time because it uses a universal set of reagents that recognizes the padlock probe backbone.

Loop-mediated amplification ("LAMP") is a biochemical reaction developed more recently. It has gained wide usage because it is an isothermal reaction, and it is relatively fast (five to twenty minutes). While it is advantageous from a speed standpoint, it is disadvantageous from a development standpoint. A typical stand-alone LAMP reaction can require a minimum of six primer sets. These sets can be time-consuming to develop, and that time can be overwhelming if many different targets need to be analyzed.

SUMMARY

Disclosed herein are devices, methods, and non-transitory computer readable media storing instructions for the amplification and identification of genetic samples that retain the advantages of both RCA and LAMP, while removing their disadvantages.

According to an exemplary embodiment of the present disclosure, a device for nucleic acid identification of material in a sample includes a microfluidics system and a heat source, where the microfluidics system further includes a movable cartridge assembly. In an embodiment, the movable cartridge assembly includes a surface configured to receive the sample at a sample location, at least one target-specific set of reagent components deposited on the surface at a target location, and at least one set of RCA-LAMP reaction components deposited on the surface at an RCA-LAMP location. Moreover, in an embodiment, the at least one target-specific set of reagent components includes: at least one target-specific padlock probe reagent component, at least one target probe-associated ligase enzyme component, and at least one target probe-associated set of ligase buffer components. In an embodiment, the at least one set of RCA-LAMP reaction components includes: at least one polymerase buffer component, at least one polymerase enzyme with strand displacement activity, a betaine additive, a TETRONIC additive, a sequence-specific probe, dNTPs, and a primer mix. Further still, in an embodiment, the primer mix includes a forward inside primer specific to a backbone of the at least one target-specific padlock probe reagent component, and a backward inside primer specific to the backbone of the at least one target-specific padlock probe reagent component.

According to another exemplary embodiment of the present disclosure, a device for biological identification of a sample includes the device of the previous embodiment, and further includes a second target-specific set of reagent components deposited on the surface at a second target location. Moreover, in an embodiment, the second target-specific set of reagent components includes: a second target-specific padlock probe reagent component, the at least one target probe-associated ligase enzyme component, and the at least one target probe-associated set of ligase buffer components. Further still, in an embodiment, the second target-specific padlock probe reagent component includes the backbone of the at least one target-specific padlock probe reagent component.

According to a further exemplary embodiment, a method for nucleic acid identification of material in a sample includes providing a microfluidics system, where the microfluidics system includes a movable cartridge assembly. In an embodiment, the movable cartridge assembly includes a surface configured to receive the sample at a sample location, at least one target-specific set of reagent components deposited on the surface at a target location, and at least one set of RCA-LAMP reaction components deposited on the surface at an RCA-LAMP location. Moreover, in an embodiment, the at least one target-specific set of reagent components includes: at least one target-specific padlock probe reagent component, at least one target probe-associated ligase enzyme component, and at least one target probe-associated set of ligase buffer components. In an embodiment, the at least one set of RCA-LAMP reaction components includes: at least one polymerase buffer component, at least one polymerase enzyme with strand displacement activity, a betaine additive, a TETRONIC additive, a sequence-specific probe, dNTPs, and a primer mix. Further still, in an embodiment, the primer mix includes a forward inside primer specific to a backbone of the at least one target-specific padlock probe reagent component, and a backward inside primer specific to the backbone of the at least one target-specific padlock probe reagent component. In an embodiment, the method further includes: transporting an aliquot of the sample received on the surface to the target location, applying heat to the target location, transporting an aliquot of RCA-LAMP reaction components on the surface to the target location, and applying heat to the target location.

According to another exemplary embodiment, a method for nucleic acid identification of material in a sample includes the method of the previous embodiment, where the movable cartridge assembly further includes a second target-specific set of reagent components deposited on the surface at a second target location. Moreover, in an embodiment, the second target-specific set of reagent components includes: a second target-specific padlock probe reagent component, the at least one target probe-associated ligase enzyme component, and the at least one target probe-associated set of ligase buffer components. Further still, in an embodiment, the second target-specific padlock probe reagent component includes the backbone of the at least one target-specific padlock probe reagent component. In an embodiment, the method further includes: transporting a second aliquot of the sample received on the surface to the second target location, applying heat to the second target location, transporting a second aliquot of RCA-LAMP reaction components on the surface to the second target location, and applying heat to the second target location.

According to a further exemplary embodiment, a non-transitory computer readable medium storing instructions that when executed by a digital microfluidics system cause the digital microfluidics system to perform a method for nucleic acid identification of material in a sample, the digital microfluidics system including a heat source, the method including transporting an aliquot of the sample received on a surface to a target location, applying heat to the target location, transporting an aliquot of RCA-LAMP reaction components on the surface to the target location, and applying heat to the target location. In an embodiment, the digital microfluidics system includes a movable cartridge assembly. In an embodiment, the movable cartridge assembly further includes a surface configured to receive the sample at a sample location, at least one target-specific set of reagent components deposited on the surface at a target location, and at least one set of RCA-LAMP reaction components deposited on the surface at an RCA-LAMP location. Moreover, in an embodiment, the at least one target-specific set of reagent components includes: at least one target-specific padlock probe reagent component, at least one target probe-associated ligase enzyme component, and at least one target probe-associated set of ligase buffer components. In an embodiment, the at least one set of RCA-LAMP reaction components includes: at least one polymerase buffer component, at least one polymerase enzyme with strand displacement activity, a betaine additive, a TETRONIC additive, a sequence-specific probe, dNTPs, and a primer mix. Further still, in an embodiment, the primer mix includes a forward inside primer specific to a backbone of the at least one target-specific padlock probe reagent component, and a backward inside primer specific to the backbone of the at least one target-specific padlock probe reagent component.

According to another exemplary embodiment, a non-transitory computer readable medium storing instructions that when executed by a digital microfluidics system cause the digital microfluidics system to perform a method for nucleic acid identification of material in a sample includes the non-transitory computer readable medium storing instructions of the previous embodiment, where the movable cartridge assembly further includes a second target-specific set of reagent components deposited on the surface at a second target location. Moreover, in an embodiment, the second target-specific set of reagent components includes: a second target-specific padlock probe reagent component, the at least one target probe-associated ligase enzyme component, and the at least one target probe-associated set of ligase buffer components. Further still, in an embodiment, the second target-specific padlock probe reagent component includes the backbone of the at least one target-specific padlock probe reagent component. In an embodiment, the method further includes: transporting a second aliquot of the sample received on the surface to the second target location, applying heat to the second target location, transporting a second aliquot of RCA-LAMP reaction components on the surface to the second target location, and applying heat to the second target location.

According to further exemplary embodiments, a device, method, or non-transitory computer readable medium storing instructions consistent with the current disclosure can be any of the previous embodiments where: (a) the ligase enzyme component is a Taq DNA ligase enzyme component; and/or (b) the set of ligase buffer components are a set of Taq DNA ligase buffer components. Alternatively, a device, method, or non-transitory computer readable medium storing instructions consistent with the current disclosure can be any of the previous embodiments where: (a) the ligase enzyme component is an RNA ligase enzyme component; and/or (b) the set of ligase buffer components are a set of RNA ligase buffer components.

According to further exemplary embodiments, a device or method consistent with the current disclosure can be any of the previous embodiments where the microfluidics system is a digital microfluidics system.

Further still, a device, method, or non-transitory computer readable medium storing instructions consistent with the current disclosure can be any of the previous embodiments where: (a) the sequence-specific probe is an oligonucleotide strand displacement probe; (b) the at least one polymerase buffer component is a Bst3 polymerase buffer component; and/or (c) the at least one polymerase enzyme with strand displacement activity is a Bst3 polymerase enzyme.

Moreover, in an embodiment, a device, method, or non-transitory computer readable medium storing instructions consistent with the current disclosure can be any of the previous embodiments where the heat source can be configured to heat fluid located at the first and/or second target location to approximately 95 degrees Celsius, and, after cooling, to approximately 65 degrees Celsius.

In a further embodiment, a device, method, or non-transitory computer readable medium storing instructions consistent with the current disclosure can be any of the previous embodiments where movable cartridge assembly is a consumable cartridge such as—but not limited to—a "single use" cartridge.

Moreover, in an embodiment, a device, method, or non-transitory computer readable medium storing instructions consistent with the current disclosure can be any of the previous embodiments further including a source of excitation radiation, and/or a camera system for monitoring possible fluorescence emanating from the surface of the movable cartridge assembly. Further still, the source of excitation radiation can be an LED configured to emit at 495 nm (or any other appropriate excitation wavelength).

In a further embodiment, a device, method, or non-transitory computer readable medium storing instructions consistent with the current disclosure can be any of the previous embodiments where the microfluidics system is configured to transport an aliquot of the sample received on the surface to the target location and is further configured to transport a second aliquot of the sample received on the surface to the second target location. Further still, the microfluidics system can be further configured to transport an aliquot of RCA-LAMP reaction components on the surface to the target location and is further configured to transport a second aliquot of RCA-LAMP reaction components on the surface to the second target location.

In a further embodiment, a device, method, or non-transitory computer readable medium storing instructions consistent with the current disclosure can be any of the previous embodiments where the at least one target-specific set of reagent components deposited on the surface at the target location are printed at the target location, and/or where the second target-specific set of reagent components deposited on the surface at the second target location are printed at the second target location. Further still, a device, method, or non-transitory computer readable medium storing instructions consistent with the current disclosure can be any of the previous embodiments where the at least one set of RCA-LAMP reaction components deposited on the surface at the RCA-LAMP location are deposited in a dried form. Such an embodiment can further include a means or step to hydrate the dried RCA-LAMP reaction components.

6

Figure 3:
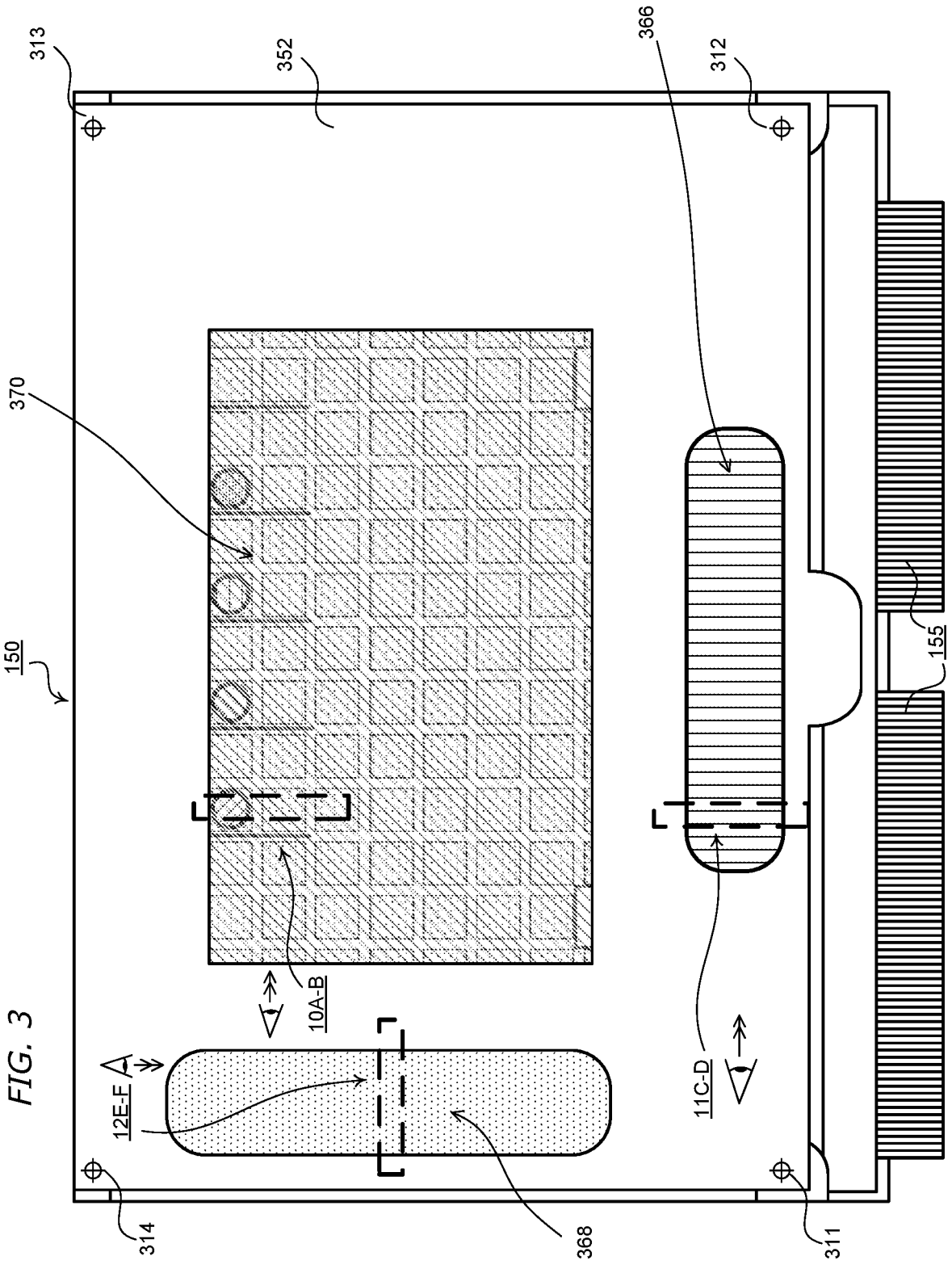
FIG. 3 illustrates a top view of an exemplary movable cartridge assembly consistent with the present disclosure.
Figure 4:
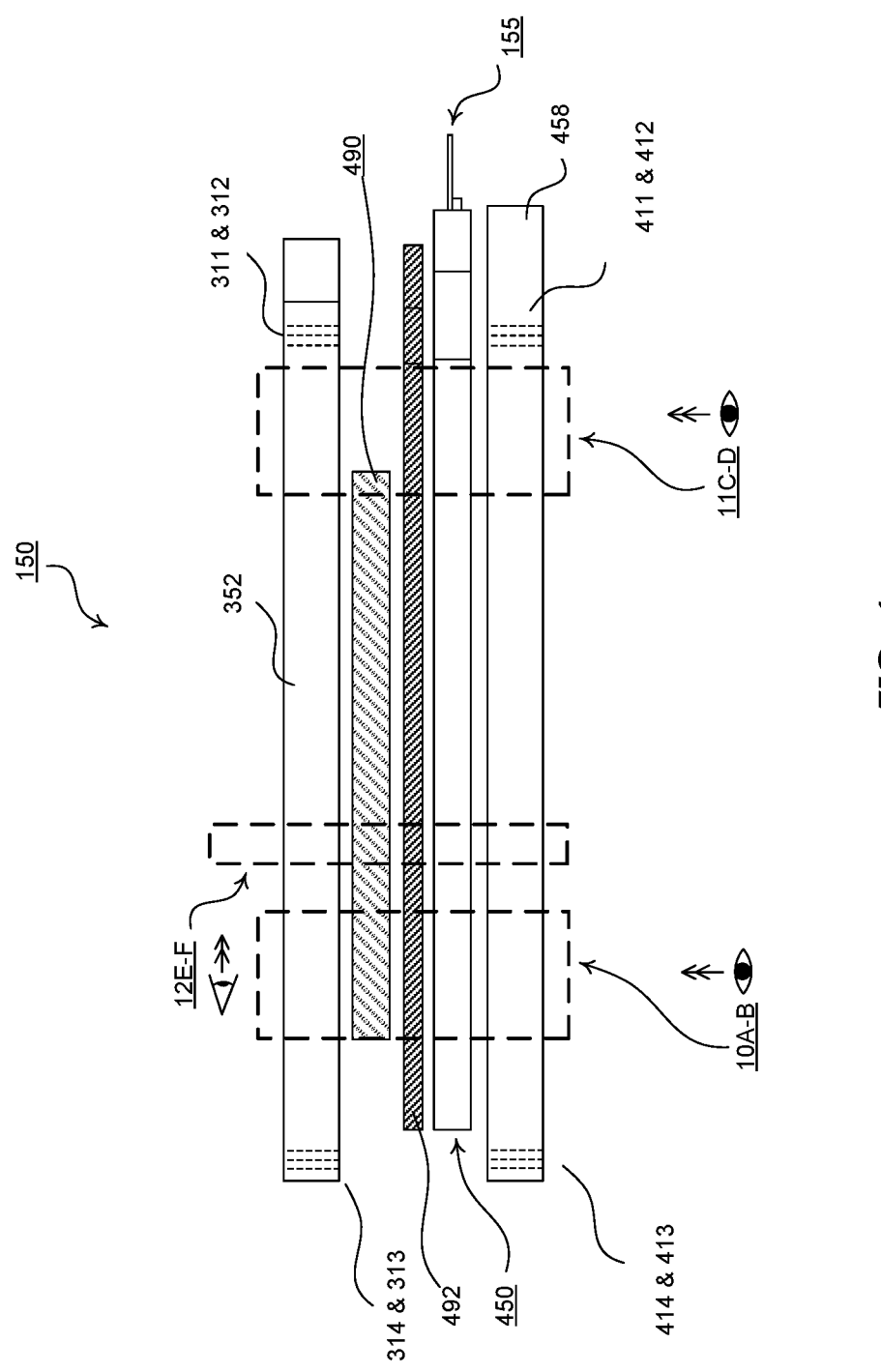
FIG. 4 illustrates an exploded cross-section view of the exemplary movable cartridge assembly of FIG. 3.
Figures 31, 32:
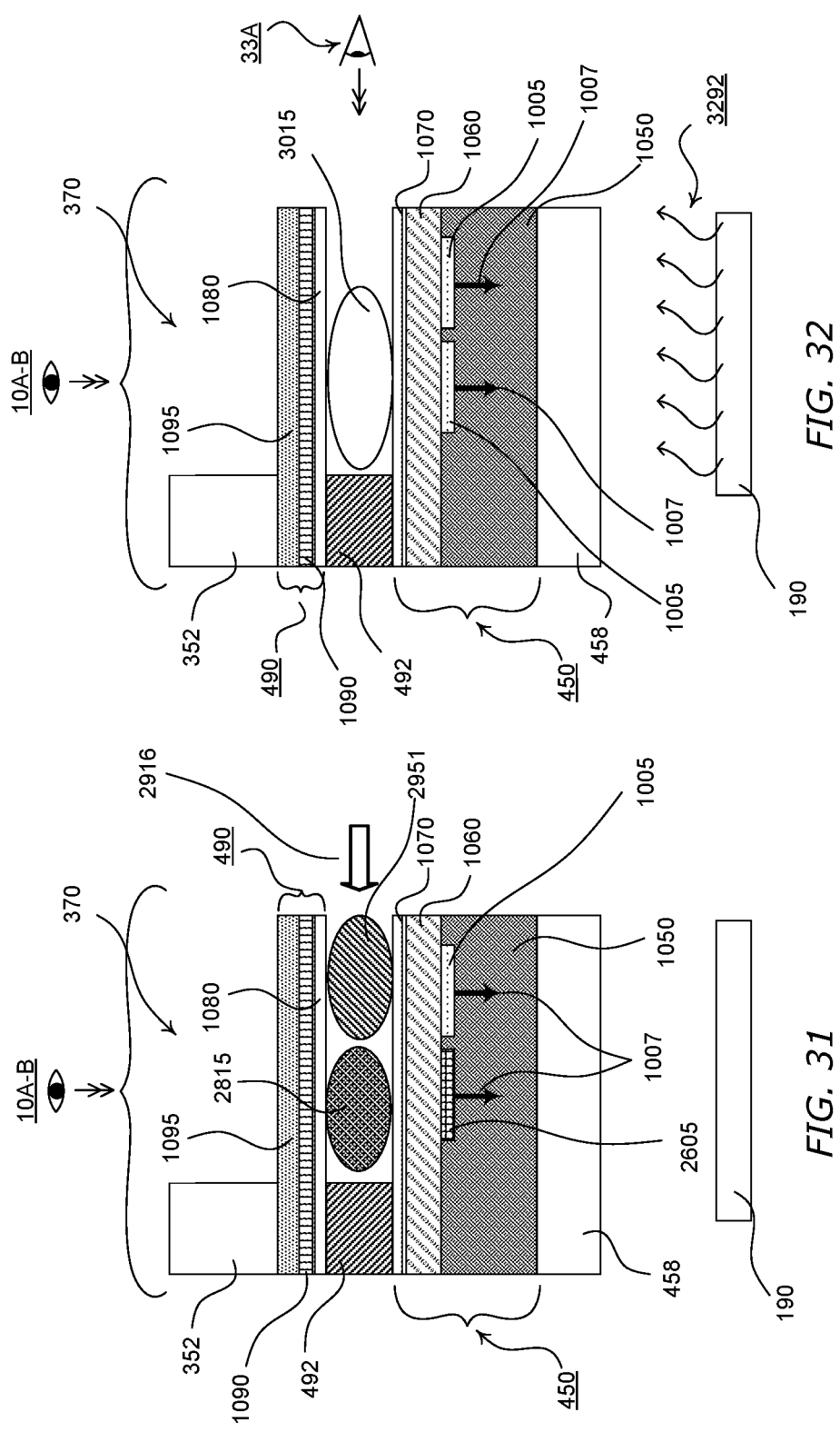

FIGS. 31-32 illustrates a cross section views of portions of the exemplary movable cartridge assembly of FIGS. 3 and 4, depicting movement, mixing, and heating of aliquots.

Figure 33:
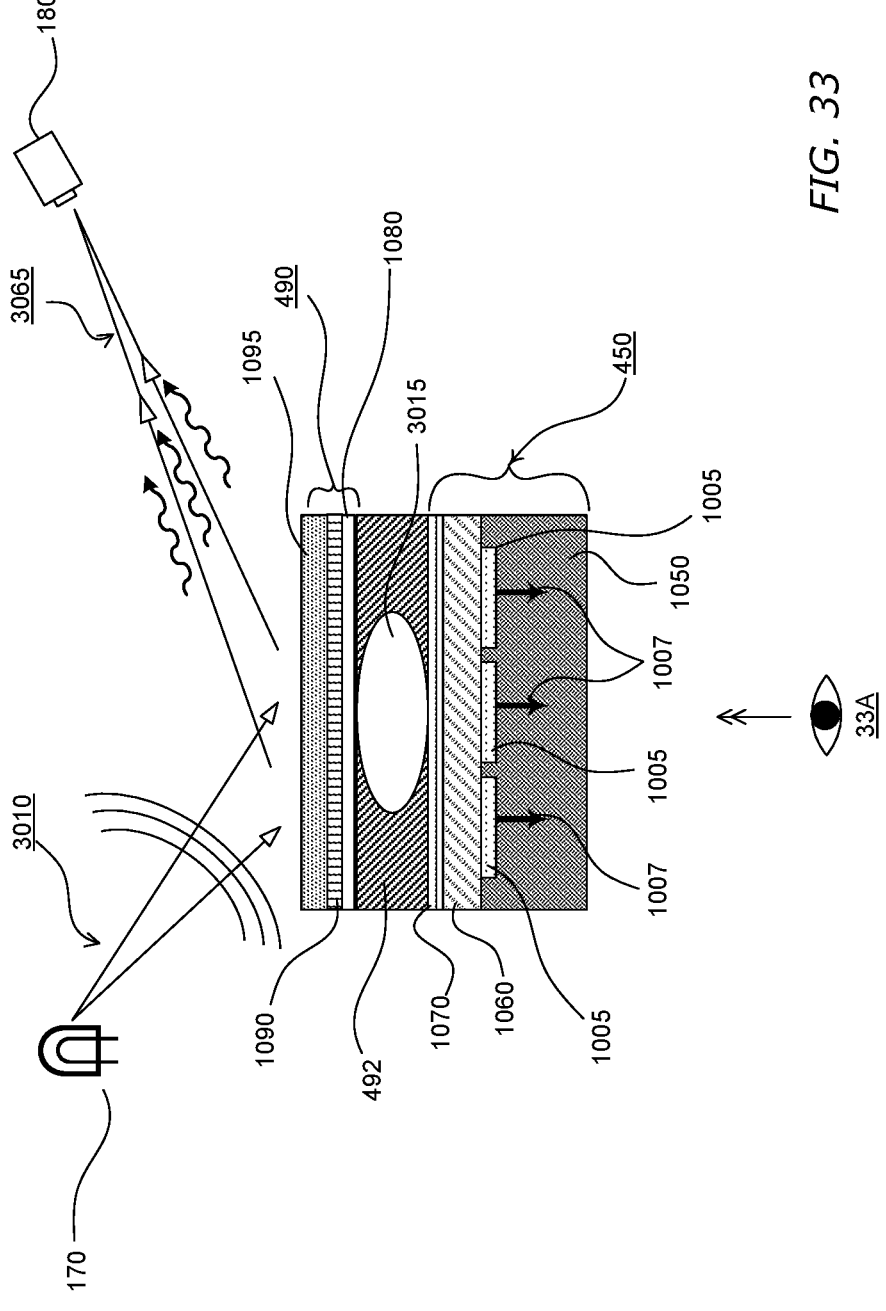

FIG. 33 illustrates another cross section view consistent with FIG. 32, depicting a mixture on the surface of the DMF Board, excitation radiation, and possible fluorescence.

Figure 34:
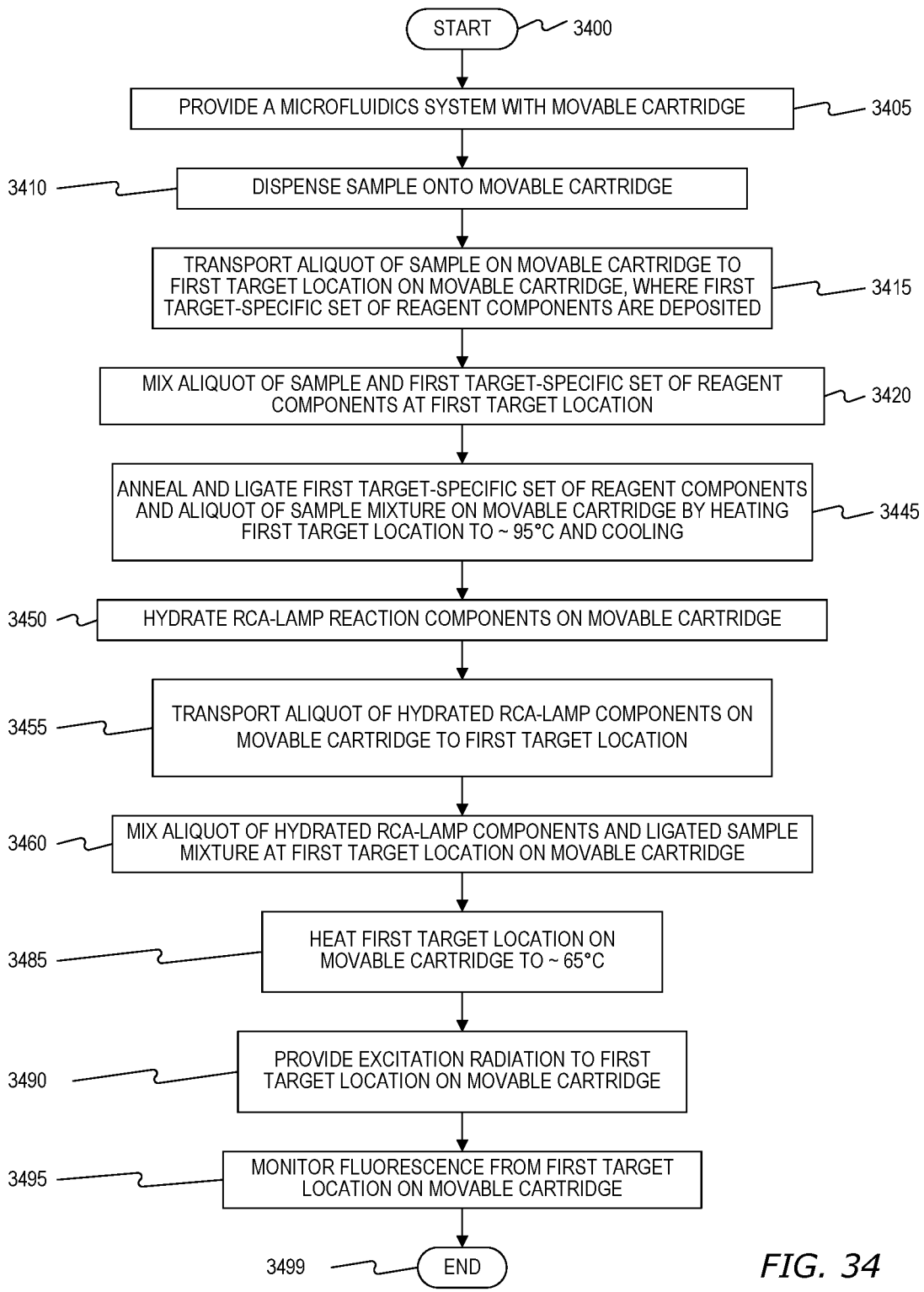
Figure 35:
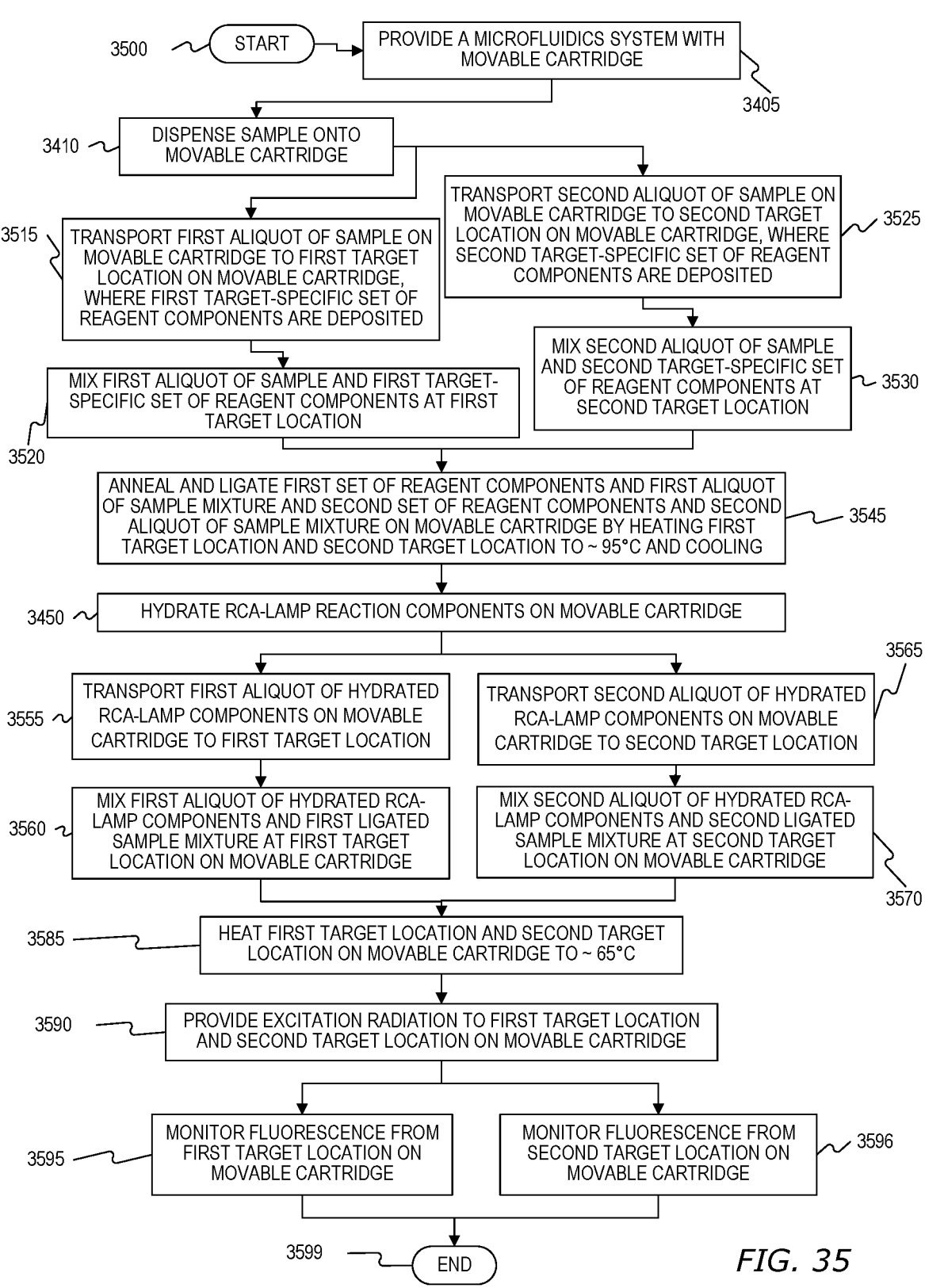

FIGS. 34 and 35 depict flowcharts of exemplary methods for nucleic acid identification of material in a sample, consistent with the present disclosure.

DETAILED DESCRIPTION

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Embodiments of the present disclosure relate generally to devices, methods, and non-transitory computer readable media storing instructions for the amplification and identification of genetic materials that may be present in samples by combining aspects of RCA and LAMP. In an embodiment, a padlock probe (an aspect of RCA) is a linear piece of single-stranded DNA and/or RNA. Its 5' and 3' arms are complementary to the genetic sequence of the target, and universal primer/probe binding sites are constructed between the arms. In the presence of the target, in an embodiment, the padlock probe arms anneal to the target genetic material in such a way that the ends of the arms become adjacent (causing the padlock probe to form a circular shape). Once it forms this circular shape, the padlock probe arms can be covalently linked with a ligase enzyme. This transforms it from a linear strand into a circular strand. Once the padlock probe is in a circular conformation, two LAMP primers (the forward inside primer, "FIP," and the backward inside primer, "BIP") can bind to it and begin creating a complementary strand that initially facilitates a hyper-branched RCA reaction. Once the first constituents of the hyper-branched RCA reaction are produced, FIP and BIP transition from an RCA reaction to a rapid LAMP reaction whose products can be detected in under twenty-five minutes. Devices, methods, and non-transitory computer-readable media storing instructions consistent with the present disclosure couples RCA and LAMP with a microfluidic device, such as a digital microfluidics ("DMF") system. One of ordinary skill in the art will appreciate that devices, methods, and non-transitory computer-readable media storing instructions consistent with the current disclosure can also be implemented using platforms based upon other kinds of microfluidic flow, including but not limited to: pressure-based, electrophoretic-based, gravitational-based, centrifugal-based, capillary-based, thermal-based, magnetophoretic, acoustic-based and electrowetting.

In accordance with embodiments of the present disclosure, there may be provided a device with a microfluidics system, such as a digital microfluidics system, and a heat source.

Figure 1:
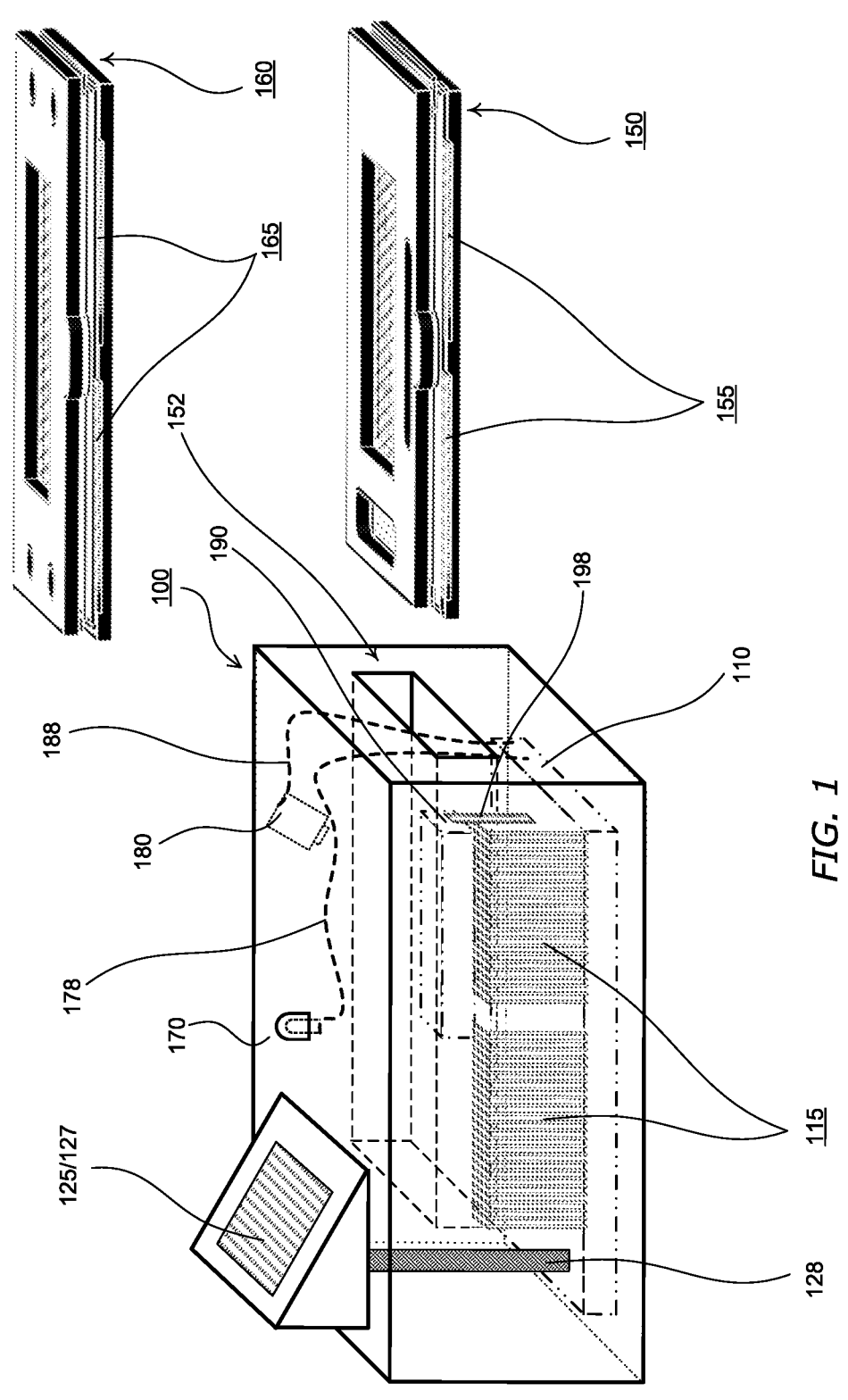
FIG. 1 illustrates an exemplary device for nucleic acid identification of material in a sample consistent with various embodiments of the present disclosure.

FIG. 1 illustrates an exemplary device 100 consistent with the present disclosure. Device 100 can include a DMF processor system 110. Connected to DMF processor system 110 are: DMF transport grid couplers 115, a coupler 128 to a combination display 125 and user interface 127, a coupler 178 to a lamp 170, a coupler 188 to a camera system 180, and a coupler 198 to a heating/cooling device 190. Device 100 also includes a slot 152 that is configured to accommodate movable cartridge assembly 150. Alternatively, or in addition, slot 152 can be configured to accommodate movable cartridge assembly 160.

Movable cartridge assembly 150 includes DMF transport grid interface 155, which is configured to couple with DMF transport grid couplers 115. Likewise, movable cartridge assembly 160 includes DMF transport grid interface 165, which is configured to couple with DMF transport grid couplers 115. One of ordinary skill in the art associated with DMF systems would appreciate that DMF transport grid interface 155 and DMF transport grid interface 165 can be consistent with PCB board edge connectors. Likewise, one of ordinary skill in the art associated with DMF systems would appreciate that DMF transport grid couplers 115 can be consistent with PCB board edge connector sockets.

Figure 2:
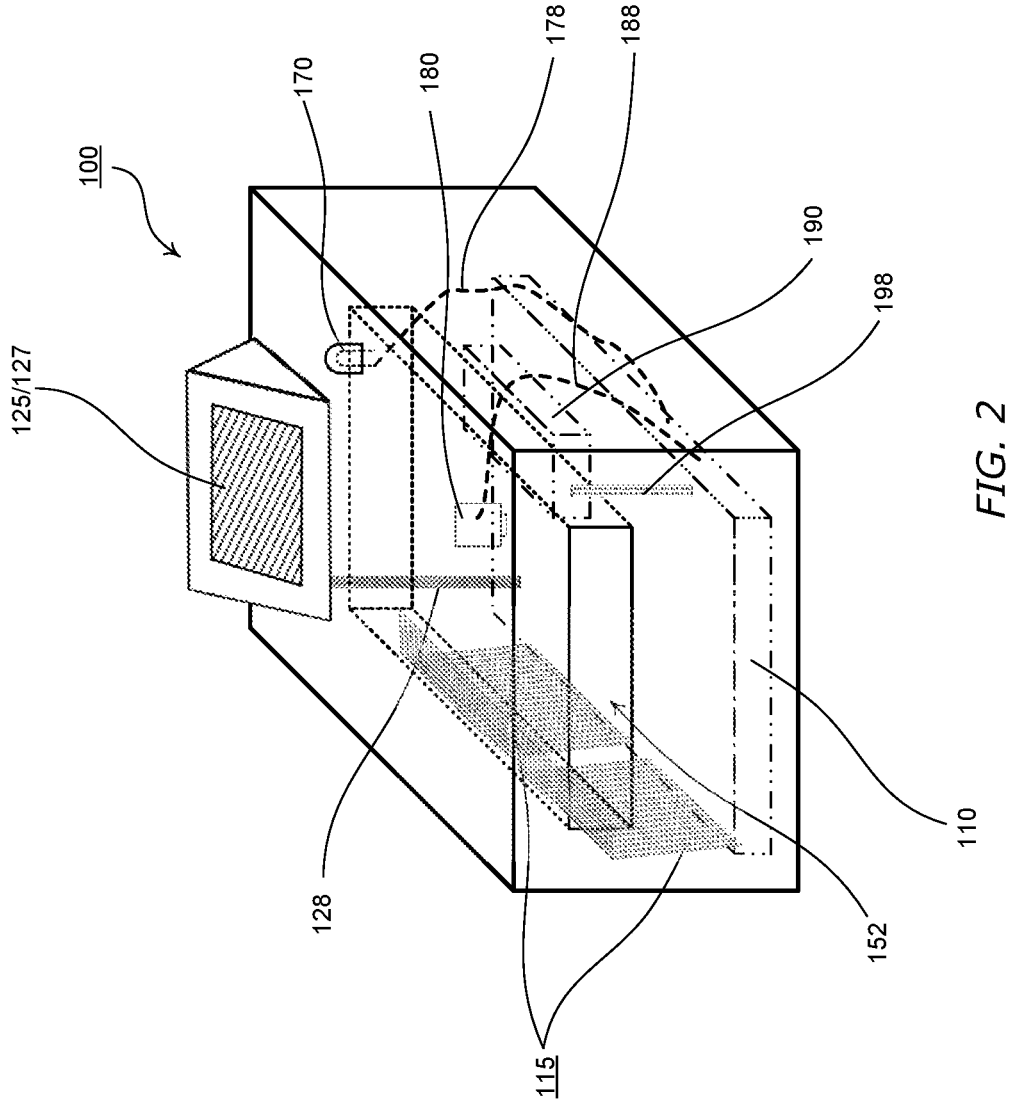
FIG. 2 illustrates a different perspective of the device of FIG. 1, without the exemplary movable cartridge assemblies.

FIG. 2 provides an alternate perspective of the device of FIG. 1 without movable cartridge assembly 150 and without movable cartridge assembly 160. Consistent with the present disclosure, lamp 170, camera system 180 and heating/cooling device 190 can be situated to one side of slot 152. Moreover, consistent with the present disclosure, heating/cooling device 190 can be situated beneath slot 152, and lamp 170 and camera system 180 can be situated above slot 152 but within the housing of device 100. Consistent with an embodiment of the present disclosure, when either movable cartridge 150 or movable cartridge 160 is situated within slot 152 (not shown in FIG. 2), lamp 170 and camera system 180 can be situated above a transparent plate (described further below) that forms a portion of movable cartridge 150 or movable cartridge 160 in a preferred embodiment. In an embodiment, camera system 180 can incorporate additional optical elements including, without limitation, filters as appropriate.

FIG. 3 illustrates a top view of exemplary movable cartridge assembly 150. Also shown in FIG. 3 are: cross-section location 10A-B with perspective indicator, cross-section location 11C-D with perspective indicator, and cross-section location 12E-F with perspective indicator. Cross-sections of movable cartridge assembly 150 associated with these locations and perspectives are shown, respectively, in FIGS. 10, 11, and 12. FIG. 3 also depicts DMF transport grid interface 155, top frame 352, and openings 311, 312, 313, and 314 for assembly fasteners. Also depicted in FIG. 3 are: opening 366 in top frame 352 to RCA-LAMP location; opening 368 in top frame 352 to sample location; and opening 370 in top frame 352 to transport and reaction area.

FIG. 4 illustrates an exploded cross-section view of movable cartridge assembly 150 of FIG. 3. Also shown in FIG. 4 are: cross-section location 10A-B with perspective indicator, cross-section location 11C-D with perspective indicator, and cross-section location 12E-F with perspective indicator. (As stated above, cross-sections of movable cartridge assembly 150 associated with these locations and perspectives are shown, respectively, in FIGS. 10, 11, and 12.) FIG. 4 also depicts (in exemplary order): top frame 352, transparent plate 490, spacer 492, DMF Board 450, and back frame 458. Again, shown as part of DMF Board 450 is DMF transport grid interface 155. As depicted in FIG. 4, openings 311, 312, 313, and 314 in top frame 352 for assembly fasteners line up with openings 411, 412, 413, and 414 (respectively) in back frame 458. Consistent with the present disclosure, openings 311, 312, 313, and 314 for assembly fasteners and openings 411, 412, 413, and 414 for assembly fasteners can accommodate fasteners (such as, but not limited to, bolts) for structurally maintaining the movable cartridge assembly 150 in the relative order shown in FIG. 4.

FIGS. 5-9 illustrate top views of components of the movable cartridge assembly of FIG. 4, where each of FIGS. 5-9 include cross-section locations 10A-B, 11C-D, and 12E-F.

Figure 5:
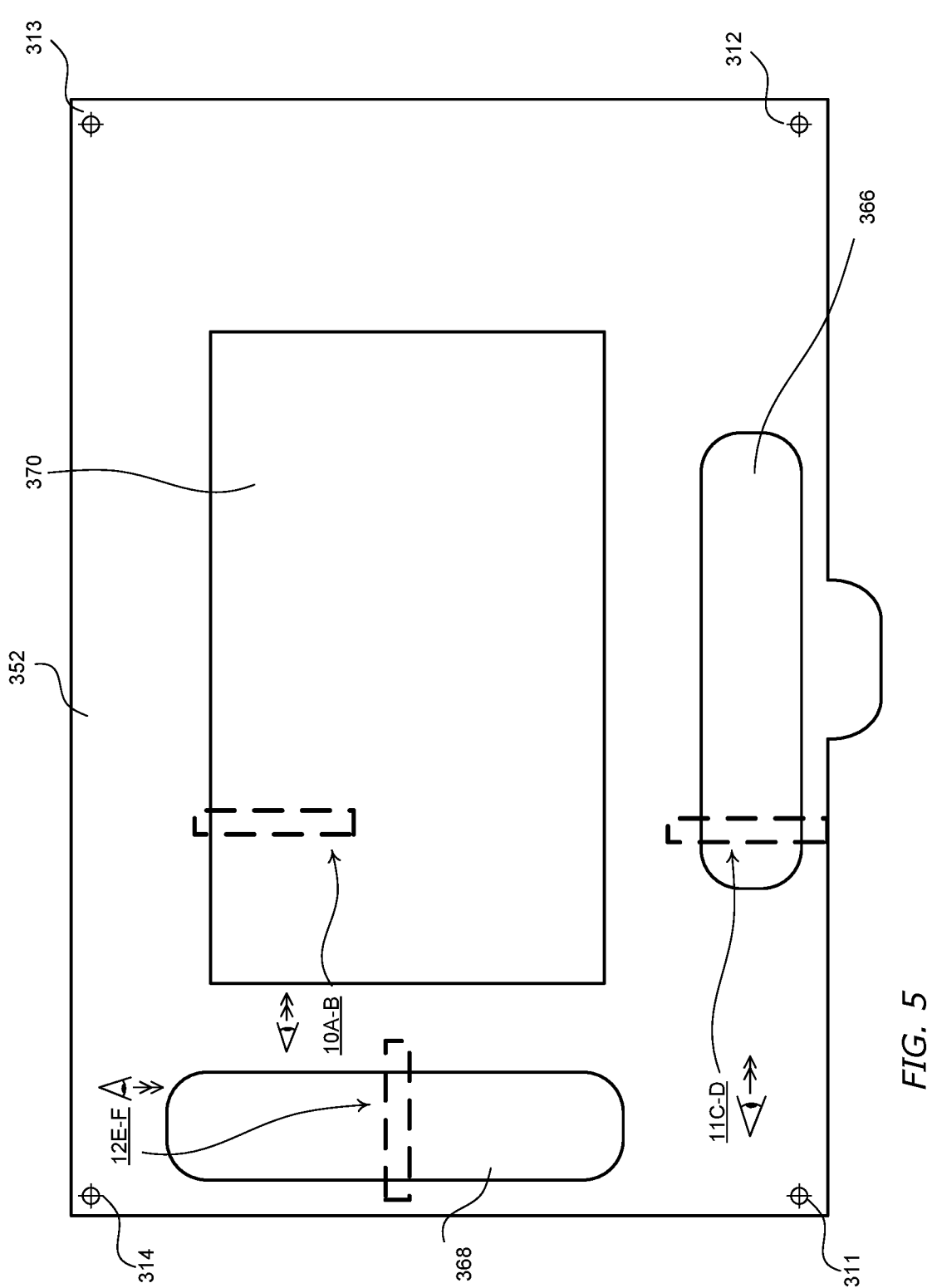
FIGS. 5-9 illustrate top views of components of the movable cartridge assembly of FIGS. 3 and 4.

FIG. 5 depicts a top view of top frame 352. Consistent with the present disclosure, top frame 352 includes opening 366 to RCA-LAMP location, opening 368 to sample location, and opening 370 to transport and reaction area. In a preferred embodiment, top frame 352 can be composed of rigid material such as, but not limited to, FR-4 that (when secured to the back frame 458—which is composed of like material) structurally maintains the relative order of the components of the movable cartridge assembly 150 and any necessary gaps between the components. In one embodiment, opening 370 can be approximately 56 mm×25 mm, opening 368 can be approximately 9 mm×39 mm, opening 366 can be approximately 45 mm×9 mm, with the entire structure of top frame 352 lying within a rectangle that can be approximately 100 mm×57 mm. In an embodiment, top frame 352 can have a thickness of the order of millimeters (i.e., approximately 1 mm if relatively flat, or ((not shown)) approximately 2 mm if shaped to envelope over, such as provide a shaped housing, for transparent plate 490, spacer 492, and DMF Board 450). In a preferred embodiment, where spacer 492 is a conductor, top frame 352 can generally be composed of non-conducting material.

Figure 6:
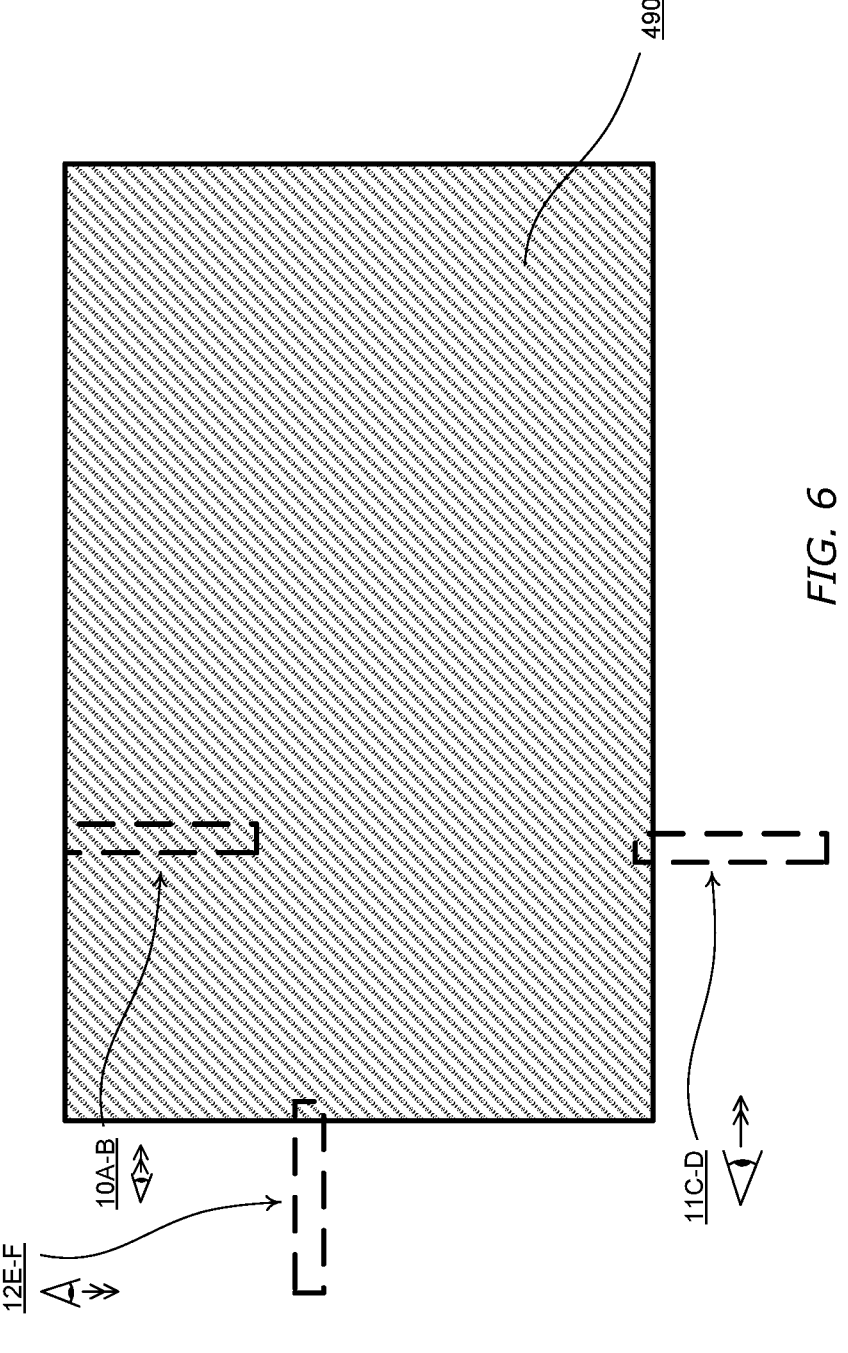

FIG. 6 depicts a top view of transparent plate 490. In an embodiment, transparent plate 490 can be formed of a glass plate with a thin layer of indium tin oxide on the "bottom" side (from the perspective of FIG. 6) to render it both transparent and conductive. Generally, in an embodiment, transparent plate 490 can be composed of any transparent conductive material. As used herein "transparent" means transmissive to incident radiation without appreciable scattering (or blocking) of the incident radiation, where the incident radiation can include any probing, excitation, and/or fluorescent radiation of interest (as described further below). In an embodiment, for example, transparent material can provide for approximately 60% or higher transmission of relevant incident radiation, and, in a preferred embodiment, highly transparent material can provide for approximately 75% or approximately 85% or higher transmission of relevant incident radiation. With regard to conductivity, in an embodiment, the sheet resistance of transparent plate 490 can be in a range from approximately 1 Ω/sq ("Ohms per square") to approximately 200 Ω/sq. Transparent plate 490 can have a thickness in the millimeter range and, in a preferred embodiment, can have a thickness of approximately 1.1 millimeters. One of ordinary skill in the art would appreciate that the bottom surface of transparent plate 490, in the transport and reaction area associated with microfluidic flow, and below any thin conductive coating, can be provided with a hydrophobic coating. In an embodiment, hydrophobic coating on transparent plate 490 can include Teflon, cytonix fluropel 1101V-FS, or Cytop CT L 809 M applied in an even method through spray, spin, dip or blot methods such that the thickness of the hydrophobic coating is between approximately 100-10,000 nanometers. One of ordinary skill in the art would also appreciate that where the bottom surface of transparent plate 490 is away from the transport and reaction area associated with microfluidic flow, and where transparent plate 490 is configured to make contact with a conductor that is part of the circuit in the digital microfluidics system responsible for controlling microfluidic flow (such as in a select region where transparent plate 490 is configured to make direct electrical contact with spacer 492, described below), the bottom surface of transparent plate 490 can be masked off so that the thin conductive layer in transparent plate 490 can make direct contact with the conductor, and thereby ensure that transparent plate 490 is part of the circuit in the digital microfluidics system.

Figure 7:
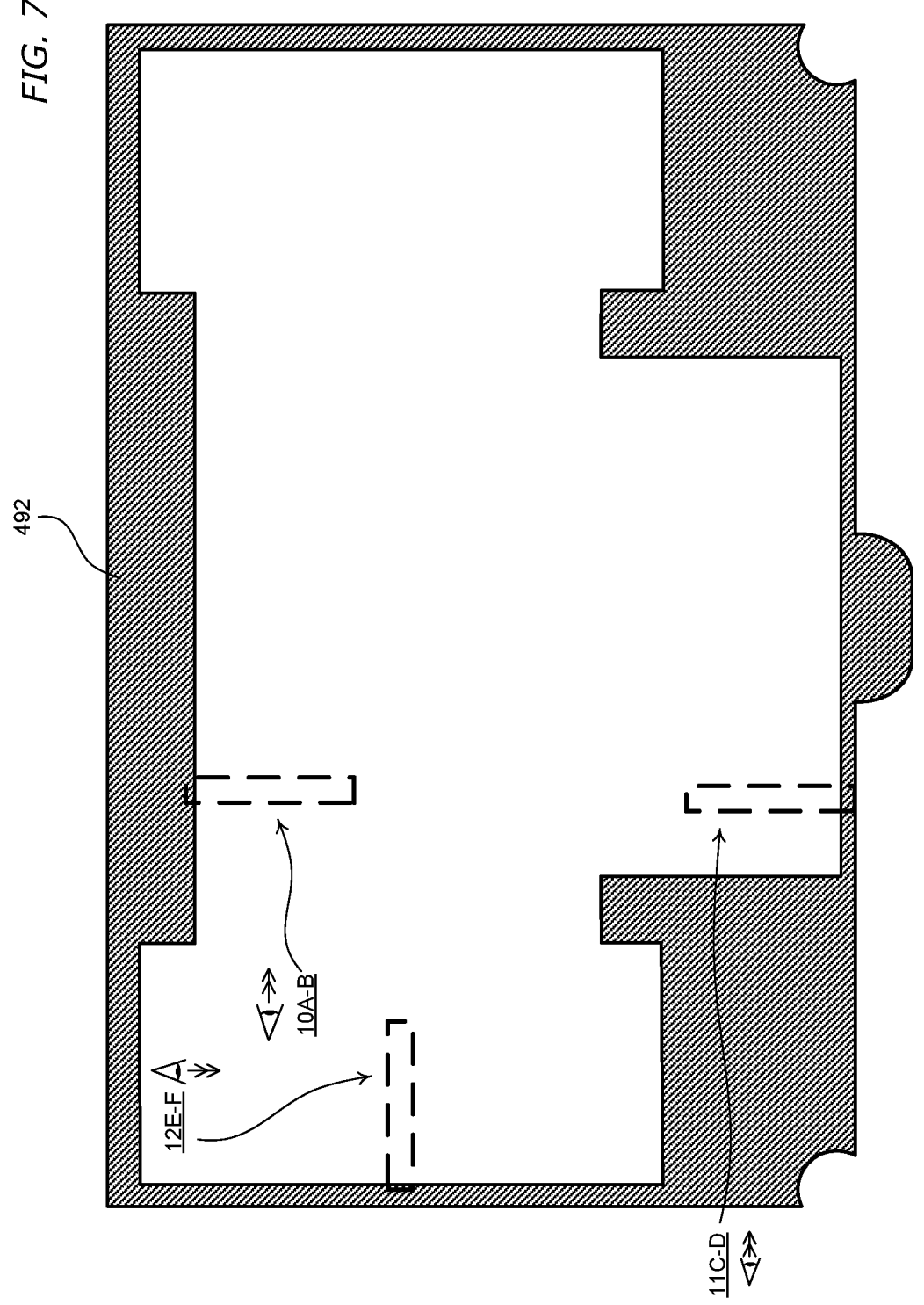

FIG. 7 depicts a top view of spacer 492. In an embodiment spacer 492 can be manufactured out of conductive material, including, but not limited to, stainless steel and copper. Furthermore, in an embodiment where the conductive electrodes in the transport and reaction area on the DMF Board 450 associated with microfluidic flow (described below), are approximately 2.6 mm×2.6 mm squares, then spacer 492 can be approximately 210-270 micrometers thick to set the appropriate gap between the "top" surface of the DMF Board 450 and the "bottom" surface of transparent plate 490. In a preferred embodiment, spacer 492 can be configured to be approximately 230 micrometers thick. One of ordinary skill in the art would appreciate that the thickness of spacer 492 (and, therefore, the gap thickness between the "top" surface of the DMF Board 450 and the "bottom" surface of transparent plate 490) scales with the size of the approximately square conductive electrodes in the transport and reaction area on the DMF Board 450 associated with microfluidic flow.

Figure 8:
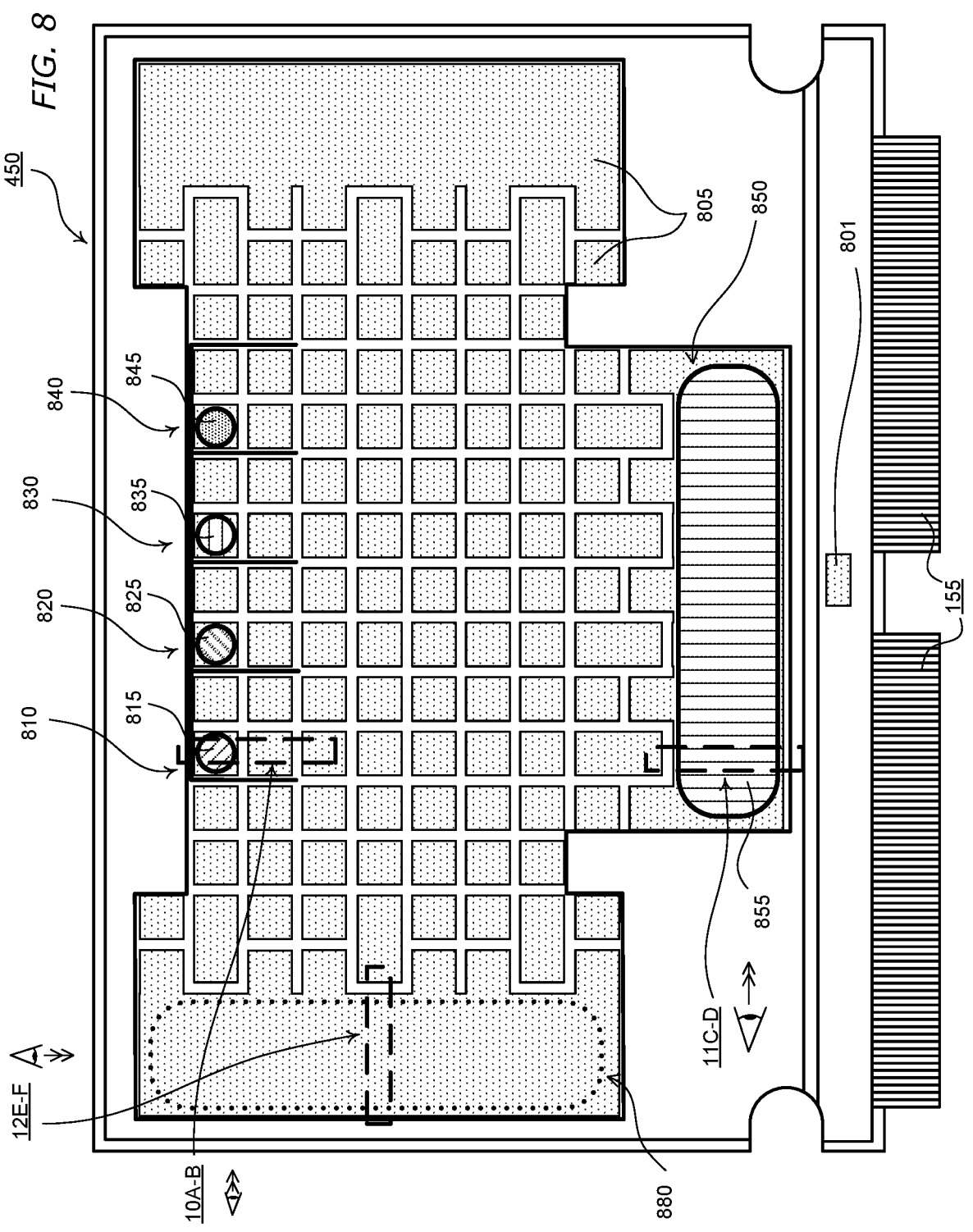

FIG. 8 depicts a top view of DMF Board 450. Consistent with the present disclosure, DMF Board 450 includes DMF transport grid interface 155. Also shown in FIG. 8 are DMF electrode locations 805. As described above, in an embodiment, the size of the electrodes at the electrode locations 805 can be approximately 2.6 mm×2.6 mm squares. One of ordinary skill in the art would appreciate that the electrodes at certain "reservoir" locations on the surface of DMF Board 450, such as sample location 880 and RCA-LAMP location 855, can generally be larger polygons composed of the base square electrode size. Moreover, one of ordinary skill in the art associated with DMF systems would appreciate the locations 805 represent grid-like locations on the surface of DMF Board 450 where fluid portions can be manipulated to move within movable cartridge assembly 150 according to the electronics of DMF Board 450 and any programming logic supported by a connected DMF processor system 110. As with the "bottom" of transparent plate 490, one of ordinary skill in the art would appreciate that the "top" surface of DMF Board 450 in the transport and reaction area, and in the "reservoir" areas described above, can be provided with a hydrophobic coating. In an embodiment, hydrophobic coating on DMF Board 450 can include Teflon, cytonix fluropel 1101V-FS, or Cytop CT L 809 M applied in an even method through spray, spin, dip or blot methods such that the thickness of the hydrophobic coating is between approximately 100-10,000 nanometers.

Also shown in FIG. 8 are first target location 810, second target location 820, third target location 830, and fourth target location 840. Located near or on an electrode location 805 in the first target location 810 is first target-specific set of reagent components 815. Likewise, located near or on an electrode location 805 in the second target location 820 is second target-specific set of reagent components 825. Located near or on an electrode location 805 in the third target location 830 is third target-specific set of reagent components 835. Similarly, located near or on an electrode location 805 in the fourth target location 840 is fourth target-specific set of reagent components 845.

In one embodiment consistent with the present disclosure, the first target-specific set of reagent components 815, the second target-specific set of reagent components 825, the third target-specific set of reagent components 835, and the fourth target-specific set of reagent components 845 are deposited on the surface of DMF Board 450 over the hydrophobic coating. Preferably, in an embodiment, the first target-specific set of reagent components 815, the second target-specific set of reagent components 825, the third target-specific set of reagent components 835, and the fourth target-specific set of reagent components 845 are deposited (and preferably printed) on the surface of DMF Board 450 in a dried state. Consistent with the present disclosure, one of ordinary skill in the art can select the reagent components to be deposited or printed at first target location 810, second target location 820, third target location 830, and fourth target location 840 (which are the padlock probes) based upon the targeted nucleic acids. The selection of reagents based upon the targeted nucleic acid is well known in the art as disclosed, for example, and without limitation, in the article "Padlock Probe Assay for Detection and Subtyping of Seasonal Influenza" by F. Neumann, et al. *Clinical Chemistry*, vol. 64, no. 12, pp. 1704-1712 (Dec. 1, 2018), where target-specific reagent components are selected in a padlock-probe-based method to identify influenza-positive samples. In an embodiment, for example, first target-specific set of reagent components 815 are selected based upon a first target nucleic acid such that the first target-specific set of reagent components 815 include the padlock probe target sequence appropriate to the first target nucleic acid. Likewise, in an embodiment, the second target-specific set of reagent components 825 are selected based upon a second target nucleic acid (which can be different from the first target nucleic acid) such that the second target-specific set of reagent components 825 include the padlock probe target sequence appropriate to the second target nucleic acid. Similarly, in an embodiment, third target-specific set of reagent components 835 are selected based upon a third target nucleic acid (which can be different from both the first target nucleic acid and the second target nucleic acid) such that the third target-specific set of reagent components 835 include the padlock probe target sequence appropriate to the third target nucleic acid. Further still, in an embodiment, fourth target-specific set of reagent components 845 are selected based upon a fourth target nucleic acid (which can be different from the first, second, and third target nucleic acids) such that the fourth target-specific set of reagent components 845 include the padlock probe target sequence appropriate to the fourth target nucleic acid.

FIG. 8 also depicts sample location 880 and RCA-LAMP location 850. In an embodiment, located on an electrode location 805 in the RCA-LAMP location 850 over the hydrophobic coating are RCA-LAMP reaction components 855. Moreover, in an embodiment consistent with the present disclosure, RCA-LAMP reaction components 855 are deposited at the RCA-LAMP location 850 in a dried state. Consistent with the present disclosure, the RCA-LAMP components 855 are "universal" reagents in the sense that the reagents in the RCA-LAMP components 855 are selected to function with each of the first target-specific set of reagent components 815, the second target-specific set of reagent components 825, the third target-specific set of reagent components 835, and the fourth target-specific set of reagent components 845 regardless of the target nucleic acid each of the target-specific set of reagent components (815, 825, 835, and 845 in the present disclosure) are specifically selected to identify using the padlock probe technique. The "universal" reagents in the RCA-LAMP components 855 include (where the reagents flagged with an asterisk, "*", are those that directly associate with the padlock probe backbone in the target-specific set of reagent components): ligase buffer; ligase enzyme*; RCA-LAMP buffer; TETRONIC; betaine; oligonucleotide strand displacement (OSD) probe*; deoxynucleotidetriphosphates (dNTPs); forward inside primer* (FIP); backward inside primer* (BIP); and Bst3* (polymerase with strand displacement activity).

Consistent with the present disclosure, the surface of DMF Board 450 at sample location 880 is accessible through both an opening in the spacer 492 and the opening 368 in top cover 352. This allows a sample to be provided on the surface of DMF Board 450 at sample location 880 through the top of movable cartridge assembly 150. Likewise, consistent with the present disclosure, the dried RCA-LAMP reaction components 855 on the surface of DMF Board 450 at RCA-LAMP sample location 850 is accessible through an opening in the spacer 492 and the opening 366 in top cover 352. This allows fluid to be provided to the surface of DMF Board 450 through the top of movable cartridge assembly 150 at RCA-LAMP location 850, in order to hydrate any dried RCA-LAMP reaction components 855. Also depicted in FIG. 8 is electrode connector 801, which, consistent with an embodiment herein, can be connected to electrical "ground" through the DMF transport grid interface 155, and can also make contact with the spacer 492 (which is conductive), and which, in turn, can make contact with a portion of the bottom of transparent plate 490, where the hydrophobic coating has not been applied (through masking, for example) so that the conductive layer portion of transparent plate 490 is thereby connected to electrical "ground."

Figure 9:
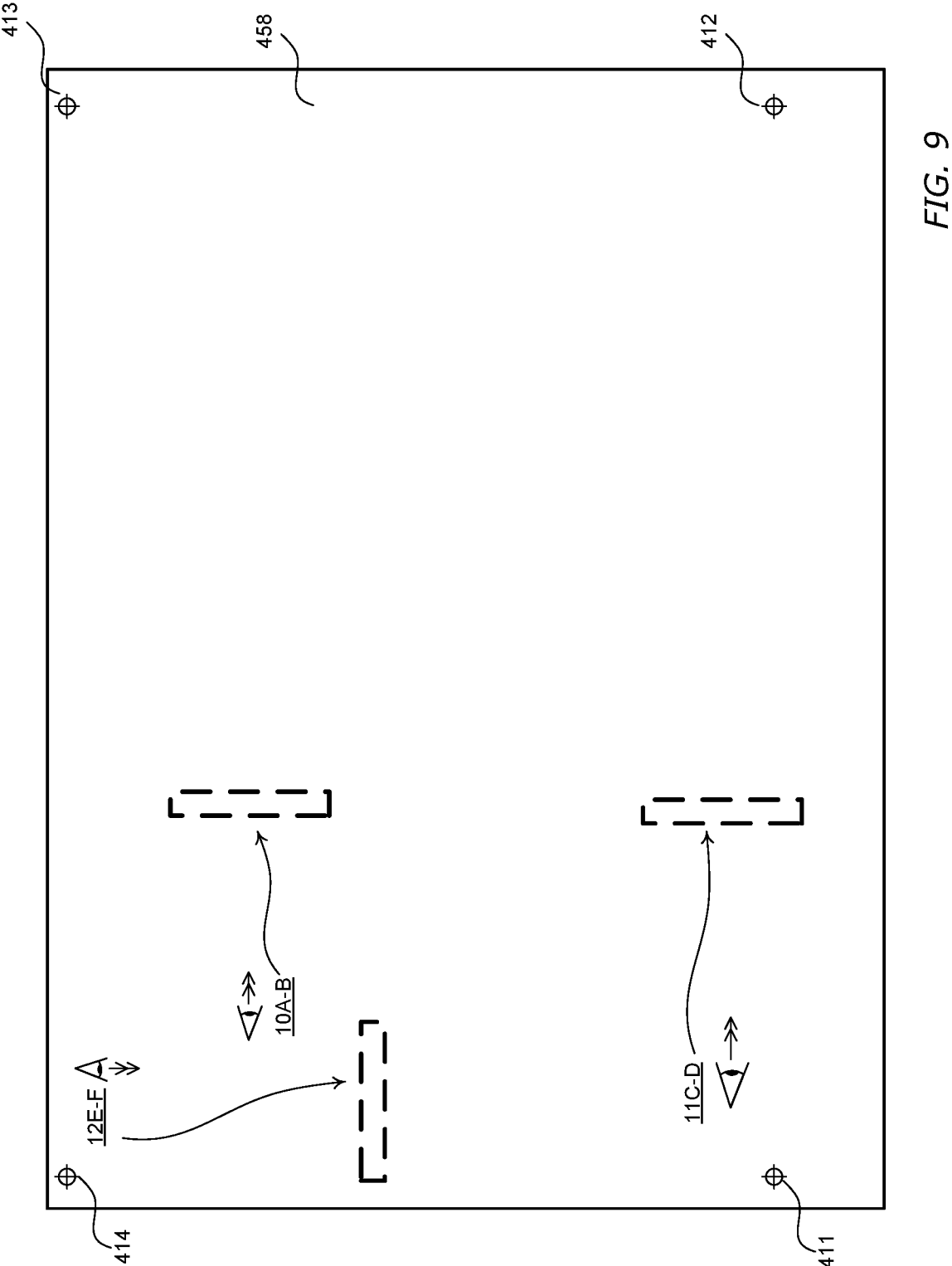

FIG. 9 depicts a top view of back frame 458. Also shown in FIG. 9 are openings 411, 412, 413, and 414, discussed earlier in connection with FIG. 4. In a preferred embodiment, back frame 458 can be composed of rigid material such as, but not limited to, FR-4 that (when secured to the top frame 352 as described above) structurally maintains the relative order of the components of the movable cartridge assembly 150 and any necessary gaps between the components. In one embodiment, the entire structure of back frame 458 lies within a rectangle that is approximately 100 mm×60 mm. In an embodiment, back frame 458 can have a thickness of the order of millimeters (i.e., approximately 1 mm if relatively flat). In a preferred embodiment, where spacer 492 is a conductor, back frame 458 can generally be composed of non-conducting material.

Figures 10, 11:
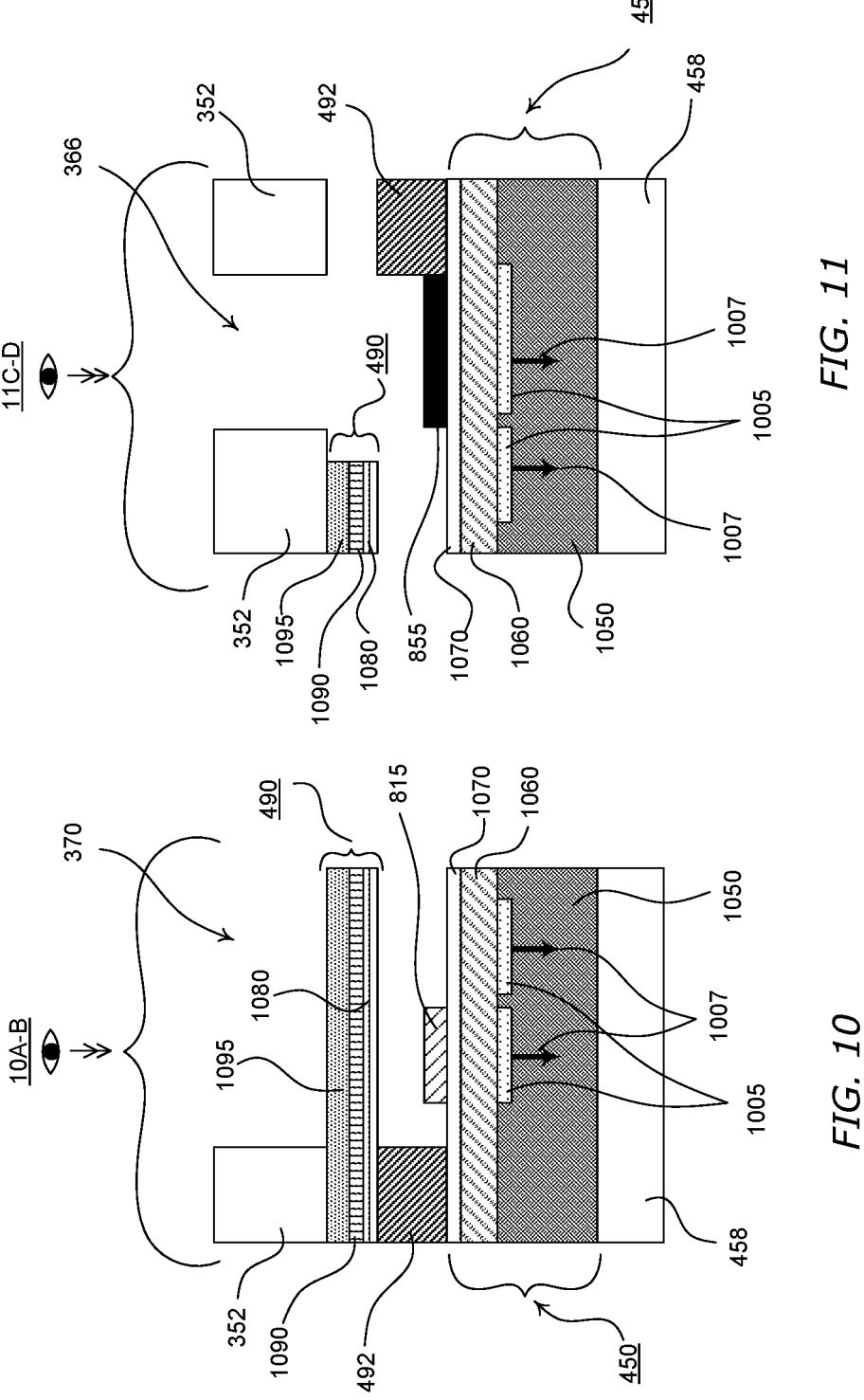
FIGS. 10-12 illustrate cross-section views of portions of the exemplary movable cartridge assembly of FIGS. 3 and 4.
Figure 12:
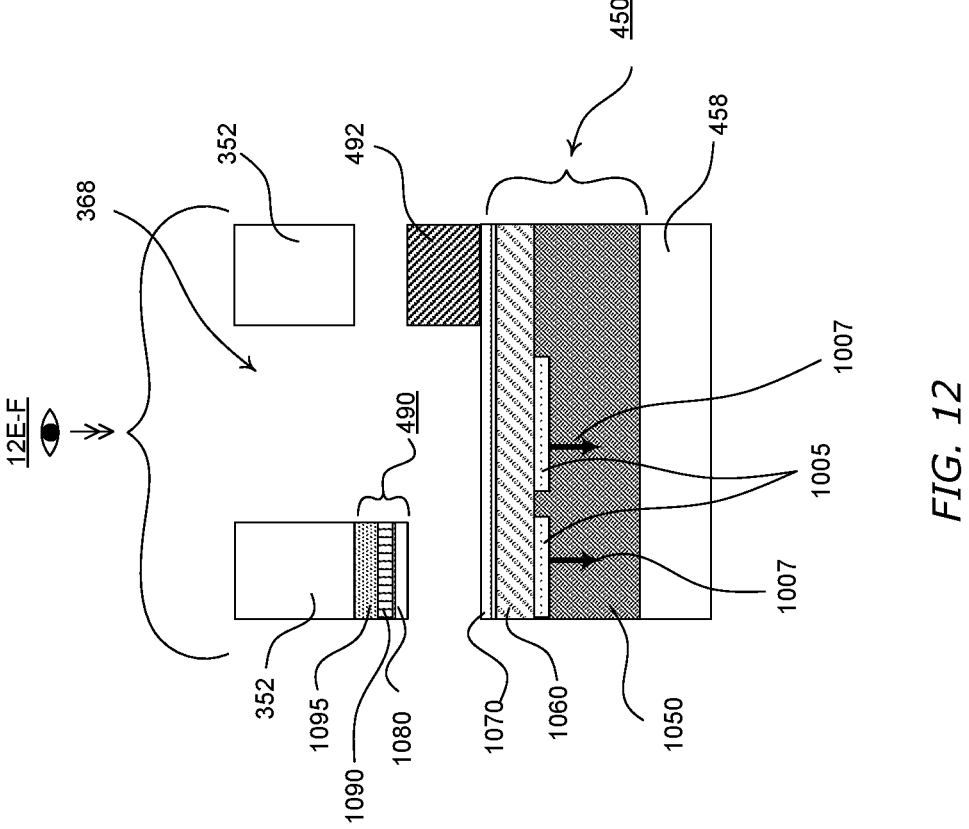

FIGS. 10-12 illustrate cross-section views of portions of the exemplary movable cartridge assembly of FIGS. 3 and 4.

FIG. 10 shows a cross-section view at location 10A-B, which includes a cross-section view of DMF Board 450 within first target location 810. Consequently, FIG. 10 includes a view of first target-specific set of reagent components 815 on hydrophobic coating 1070. DMF Board 450 further includes dielectric 1060, substrate 1050, electrodes 1005 and electrode connectors 1007 (where electrode connectors 1007, in turn, connect to the DMF transport grid interface 155 and are under control of DMF processor system 110). Spacer 492 is shown, as well as transparent plate 490, which can include glass layer 1095, conductive layer 1090, and hydrophobic coating 1080. Dielectric 1060 can include material such as, but not limited to, parylene-C and can be formed in a layer with a thickness from approximately 2-20 microns.

FIG. 11 shows a cross-section view at location 11C-D, which includes a cross-section view of DMF Board 450 within RCA-LAMP location 850. Consequently, FIG. 11 includes a view of RCA-LAMP reaction components 855 on hydrophobic coating 1070. As in FIG. 10, DMF Board 450 further includes dielectric 1060, substrate 1050, electrodes 1005 and electrode connectors 1007 (where electrode connectors 1007, in turn, connect to the DMF transport grid interface 155, and are under control of DMF processor system 110). Spacer 492 is shown, as well as transparent plate 490, which includes glass layer 1095, conductive layer 1090, and hydrophobic coating 1080.

FIG. 12 shows a cross-section view at location 12E-F, which includes a cross-section view of DMF Board 450 within sample location 880. As in FIGS. 10 and 11, DMF Board 450 further includes dielectric 1060, substrate 1050, electrodes 1005 and electrode connectors 1007 (where electrode connectors 1007, in turn, connect to the DMF transport grid interface 155, and are under control of DMF processor system 110). Spacer 492 is shown, as well as transparent plate 490, which includes glass layer 1095, conductive layer 1090, and hydrophobic coating 1080.

Figure 13:
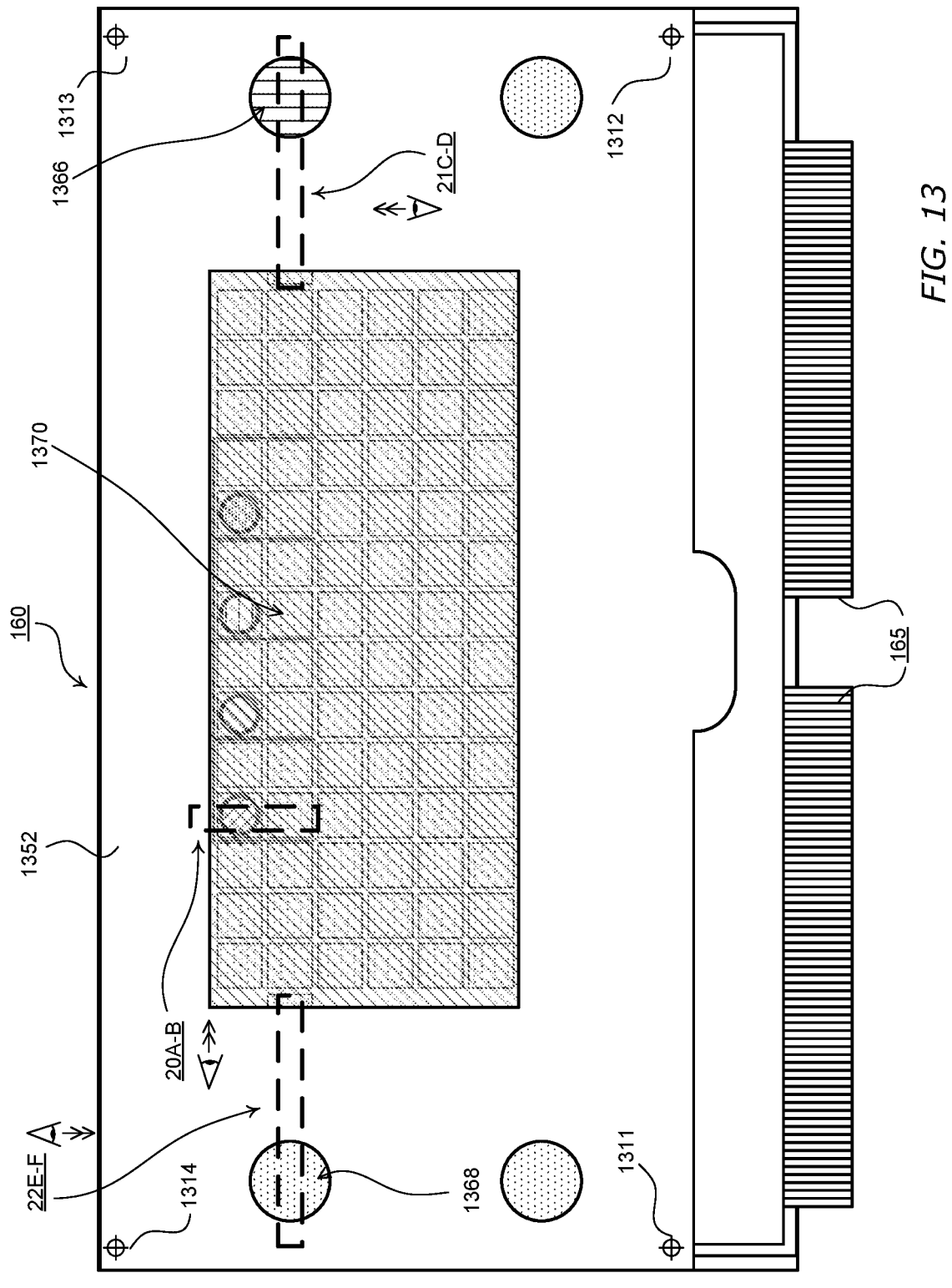
FIG. 13 illustrates a top view of a further exemplary movable cartridge assembly consistent with the present disclosure.

FIG. 13 illustrates a top view of exemplary movable cartridge assembly 160. Also shown in FIG. 13 are: cross-section location 20A-B with perspective indicator, cross-section location 21C-D with perspective indicator, and cross-section location 22E-F with perspective indicator. Cross-sections of movable cartridge assembly 160 associated with these locations and perspectives are shown, respectively, in FIGS. 20, 21, and 22. FIG. 13 also depicts DMF transport grid interface 165, top frame 1352, and openings 1311, 1312, 1313, and 1314 for assembly fasteners. Also depicted in FIG. 13 are: opening 1366 in top frame 1352 to RCA-LAMP location; opening 1368 in top frame 1352 to sample location; and opening 1370 in top frame 1352 to transport and reaction area.

Figure 14:
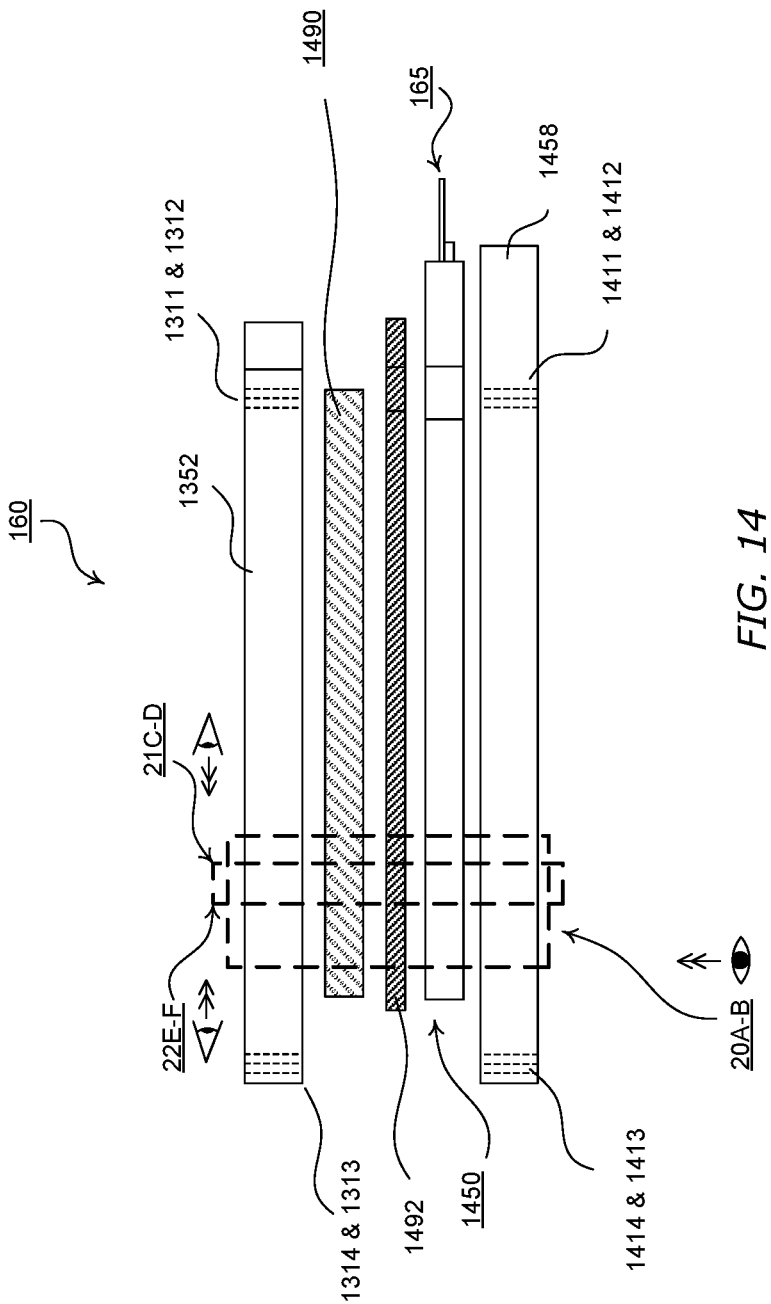
FIG. 14 illustrates an exploded cross-section view of the exemplary movable cartridge assembly of FIG. 13.

FIG. 14 illustrates an exploded cross-section view of movable cartridge assembly 160 of FIG. 13. Also shown in FIG. 14 are: cross-section location 20A-B with perspective indicator, cross-section location 21C-D with perspective indicator, and cross-section location 22E-F with perspective indicator. (As stated above, cross-sections of movable cartridge assembly 160 associated with these locations and perspectives are shown, respectively, in FIGS. 20, 21, and 22.) FIG. 14 also depicts (in exemplary order): top frame 1352, transparent plate 1490, spacer 1492, DMF Board 1450, and back frame 1458. Again, shown as part of DMF Board 1450 is DMF transport grid interface 165. As depicted in FIG. 14, openings 1311, 1312, 1313, and 1314 in top frame 1352 for assembly fasteners line up with openings 1411, 1412, 1413, and 1414 (respectively) in back frame 1458. Consistent with the present disclosure, openings 1311, 1312, 1313, and 1314 for assembly fasteners and openings 1411, 1412, 1413, and 1414 for assembly fasteners can accommodate fasteners (such as, but not limited to, bolts) for structurally maintaining the movable cartridge assembly 160 in the relative order shown in FIG. 14.

FIGS. 15-19 illustrate top views of components of the movable cartridge assembly of FIG. 14, where each of FIGS. 15-19 include cross-section locations 20A-B, 21C-D, and 22E-F.

Figure 15:
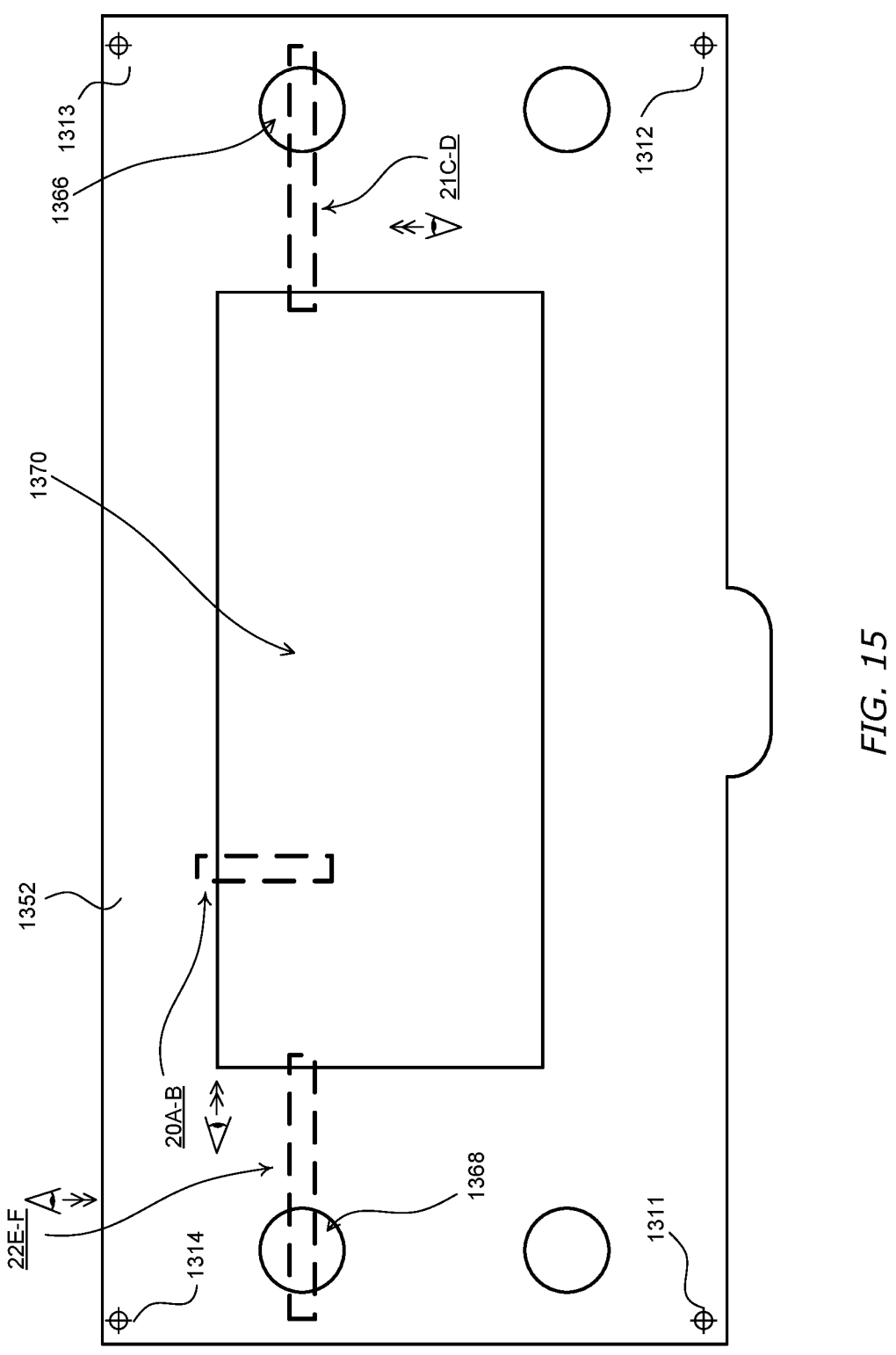
FIGS. 15-19 illustrate top views of components of the movable cartridge assembly of FIGS. 13 and 14.

FIG. 15 depicts a top view of top frame 1352. Consistent with the present disclosure, top frame 1352 includes opening 1366 to RCA-LAMP location, opening 1368 to sample location, and opening 1370 to transport and reaction area. In a preferred embodiment, top frame 1352 can be composed of rigid material such as, but not limited to, FR-4 that (when secured to the back frame 1458—which is composed of like material) structurally maintains the relative order of the components of the movable cartridge assembly 160 and any necessary gaps between the components. In one embodiment, opening 1370 can be approximately 56 mm×25 mm, opening 1368 can be approximately 9 mm×9 mm, opening 1366 can be approximately 9 mm×9 mm, with the entire structure of top frame 1352 lying within a rectangle that can be approximately 100 mm×57 mm. In an embodiment, top frame 1352 can have a thickness of the order of millimeters (i.e., approximately 1 mm if relatively flat, or ((not shown)) approximately 2 mm if shaped to envelope over, such as provide a shaped housing, for transparent plate 1490, spacer 1492, and DMF Board 1450). In a preferred embodiment, where spacer 1492 is a conductor, top frame 1352 can generally be composed of non-conducting material.

Figure 16:
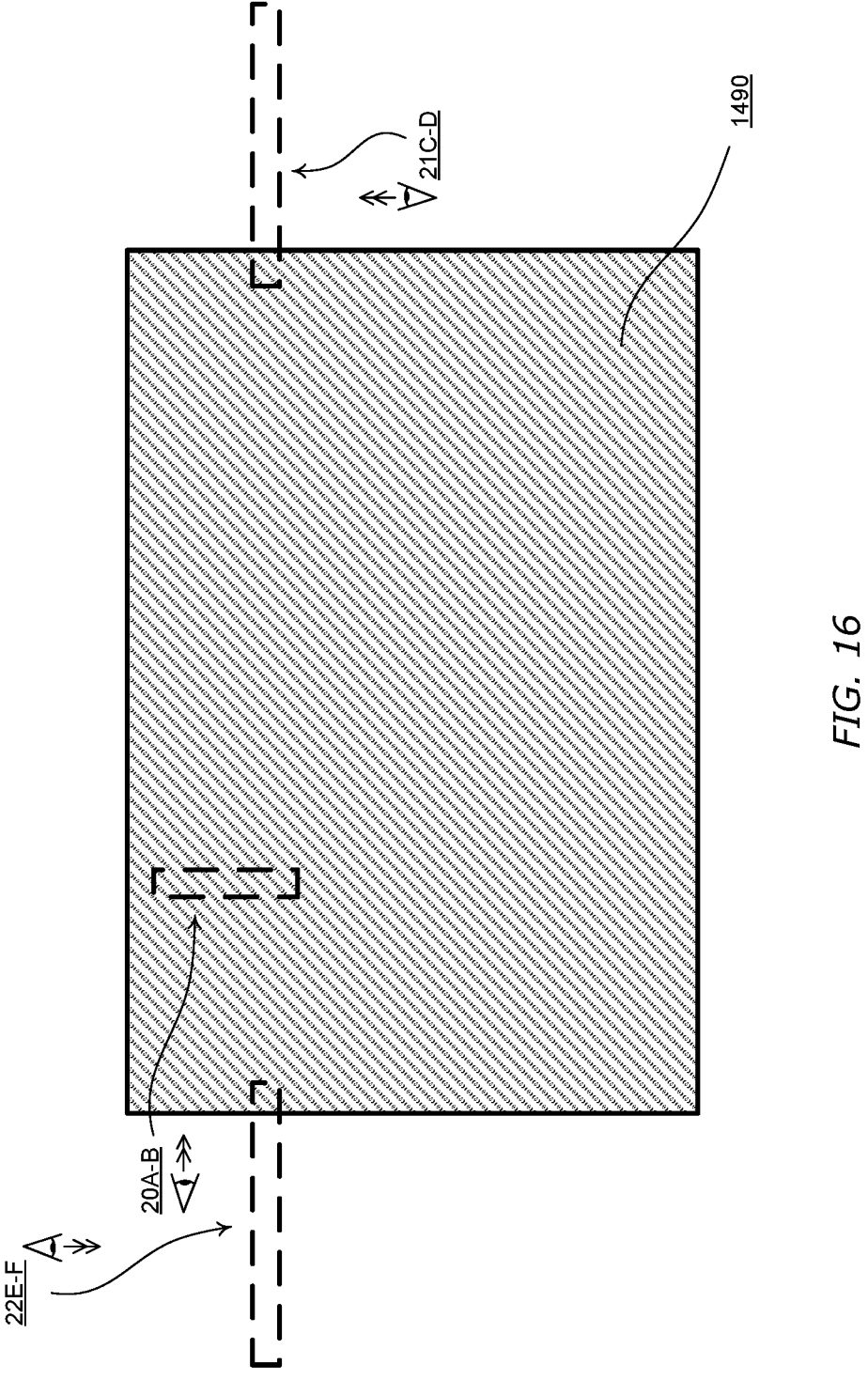

FIG. 16 depicts a top view of transparent plate 1490. In an embodiment, transparent plate 1490 can be formed of a glass plate with a thin layer of indium tin oxide on the "bottom" side (from the perspective of FIG. 16) to render it both transparent and conductive. Generally, in an embodiment, transparent plate 1490 can be composed of any transparent conductive material. In an embodiment, for example, transparent material can provide for approximately 60% or higher transmission of relevant incident radiation, and, in a preferred embodiment, highly transparent material can provide for approximately 75% or approximately 85% or higher transmission of relevant incident radiation. With regard to conductivity, in an embodiment, the sheet resistance of transparent plate 1490 can be in a range from approximately 1 $\Omega$/sq to approximately 200 $\Omega$/sq. Transparent plate 1490 can have a thickness in the millimeter range and, in a preferred embodiment, can have a thickness of approximately 1.1 millimeters. One of ordinary skill in the art would appreciate that the bottom surface of transparent plate 1490, in the transport and reaction area associated with microfluidic flow, and below any thin conductive coating, can be provided with a hydrophobic coating. In an embodiment, hydrophobic coating on transparent plate 1490 can include Teflon, cytonix fluropel 1101V-FS, or Cytop CT L 809 M applied in an even method through spray, spin, dip or blot methods such that the thickness of the hydrophobic coating is between approximately 100-10,000 nanometers. One of ordinary skill in the art would also appreciate that where the bottom surface of transparent plate 1490 is away from the transport and reaction area associated with microfluidic flow, and where transparent plate 1490 is configured to make contact with a conductor that is part of the circuit in the digital microfluidics system responsible for controlling microfluidic flow (such as in a select region where transparent plate 1490 is configured to make direct electrical contact with spacer 1492, described below), the bottom surface of transparent plate 1490 can be masked off so that the thin conductive layer in transparent plate 1490 can make direct contact with the conductor, and thereby ensure that transparent plate 1490 is part of the circuit in the digital microfluidics system.

Figure 17:
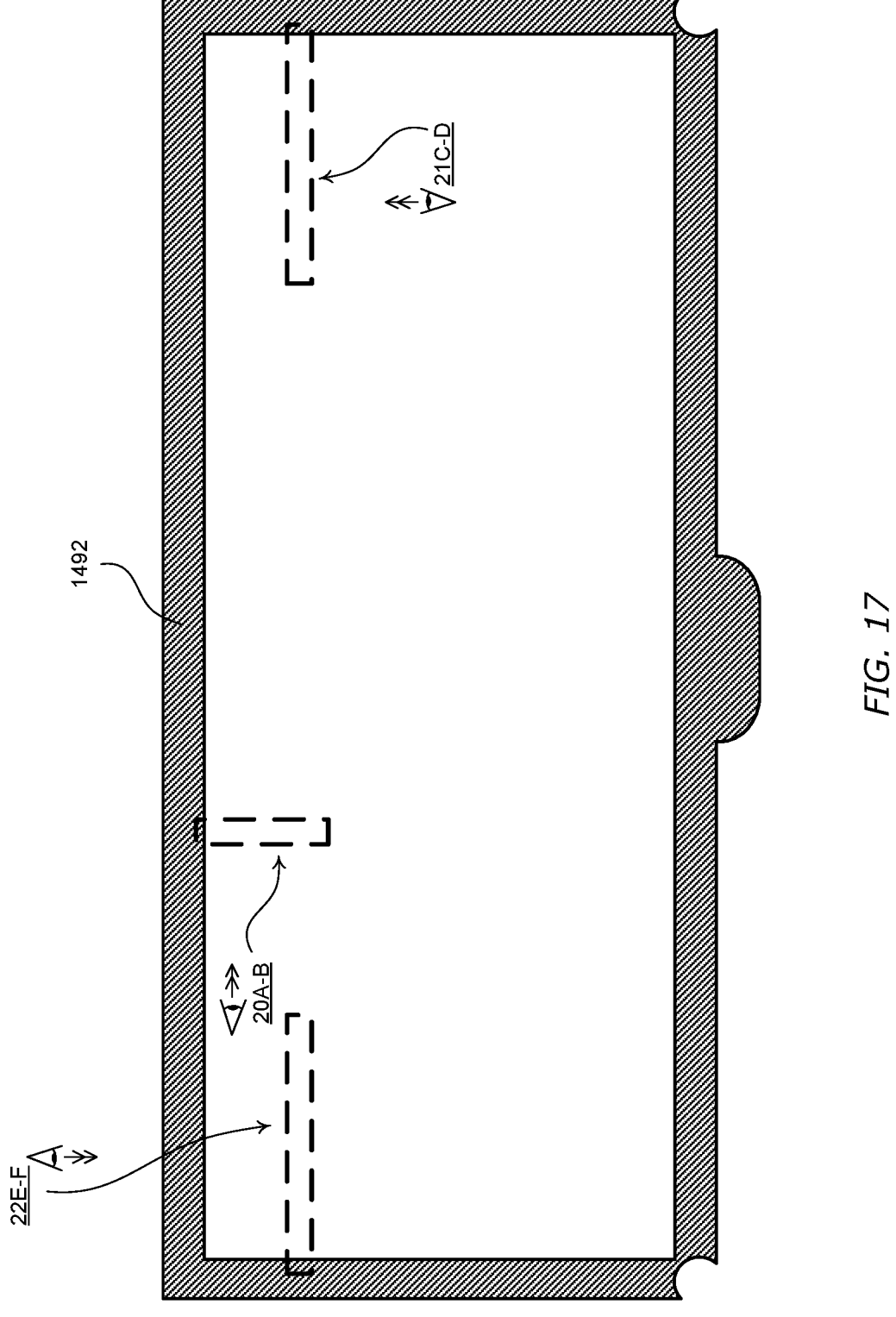

FIG. 17 depicts a top view of spacer 1492. In an embodiment spacer 1492 can be manufactured out of conductive material, including, but not limited to, stainless steel and copper. Furthermore, in an embodiment where the conductive electrodes in the transport and reaction area on the DMF Board 1450 associated with microfluidic flow (described below), are approximately 2.6 mm×2.6 mm squares, then spacer 1492 can be approximately 210-270 micrometers thick to set the appropriate gap between the "top" surface of the DMF Board 1450 and the "bottom" surface of transparent plate 1490. In a preferred embodiment, spacer 1492 can be configured to be approximately 230 micrometers thick. One of ordinary skill in the art would appreciate that the thickness of spacer 1492 (and, therefore, the gap thickness between the "top" surface of the DMF Board 1450 and the "bottom" surface of transparent plate 1490) scales with the size of the approximately square conductive electrodes in the transport and reaction area on the DMF Board 1450 associated with microfluidic flow.

Figure 18:
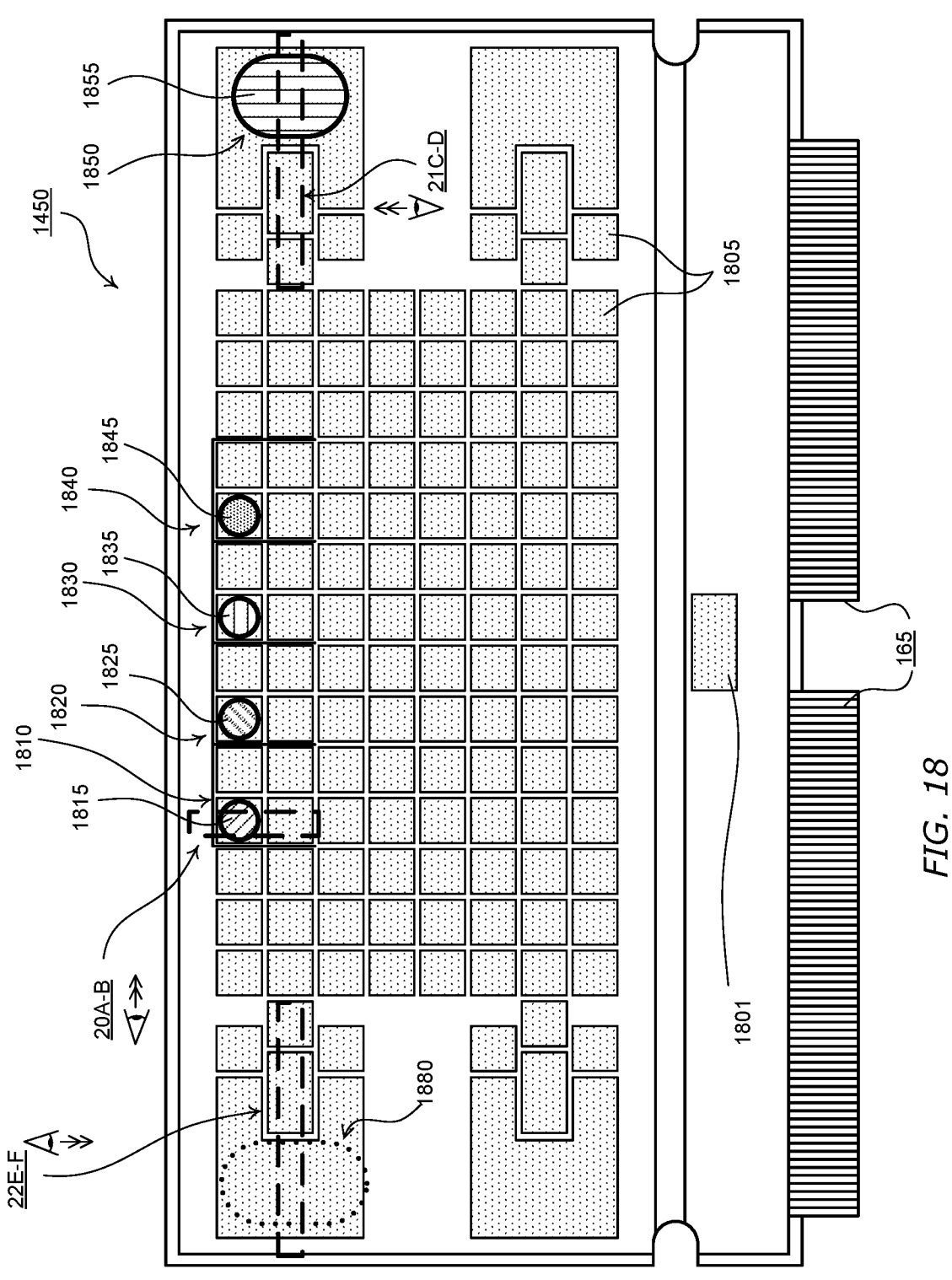

FIG. 18 depicts a top view of DMF Board 1450. Consistent with the present disclosure, DMF Board 1450 includes DMF transport grid interface 165. Also shown in FIG. 8 are DMF electrode locations 1805. As described above, in an embodiment, the size of the electrodes at the electrode locations 1805 can be approximately 2.6 mm×2.6 mm squares. One of ordinary skill in the art would appreciate that the electrodes at certain "reservoir" locations on the surface of DMF Board 1450, such as sample location 1880 and RCA-LAMP location 1855, can generally be larger polygons composed of the base square electrode size. Moreover, one of ordinary skill in the art associated with DMF systems would appreciate the locations 1805 represent grid-like locations on the surface of DMF Board 1450 where fluid portions can be manipulated to move within movable cartridge assembly 160 according to the electronics of DMF Board 1450 and any programming logic supported by a connected DMF processor system 110. As with the "bottom" of transparent plate 1490, one of ordinary skill in the art would appreciate that the "top" surface of DMF Board 1450 in the transport and reaction area, and in the "reservoir" areas described above, can be provided with a hydrophobic coating. In an embodiment, hydrophobic coating on DMF Board 1450 can include Teflon, cytonix fluropel 1101V-FS, or Cytop CT L 809 M applied in an even method through spray, spin, dip or blot methods such that the thickness of the hydrophobic coating is between approximately 100-10,000 nanometers.

Also shown in FIG. 18 are first target location 1810, second target location 1820, third target location 1830, and fourth target location 1840. Located near or on an electrode location 1805 in the first target location 1810 is first target-specific set of reagent components 1815. Likewise, located near or on an electrode location 1805 in the second target location 1820 is second target-specific set of reagent components 1825. Located near or on an electrode location 1805 in the third target location 1830 is third target-specific set of reagent components 1835. Similarly, located near or on an electrode location 1805 in the fourth target location 1840 is fourth target-specific set of reagent components 1845.

In one embodiment consistent with the present disclosure, the first target-specific set of reagent components 1815, the second target-specific set of reagent components 1825, the third target-specific set of reagent components 1835, and the fourth target-specific set of reagent components 1845 are deposited on the surface of DMF Board 1450 over the hydrophobic coating. Preferably, in an embodiment, the first target-specific set of reagent components 1815, the second target-specific set of reagent components 1825, the third target-specific set of reagent components 1835, and the fourth target-specific set of reagent components 1845 are deposited (and preferably printed) on the surface of DMF Board 1450 in a dried state. Consistent with the present disclosure, one of ordinary skill in the art can select the reagent components to be deposited or printed at first target location 1810, second target location 1820, third target location 1830, and fourth target location 1840 (which are the padlock probes) based upon the targeted nucleic acids. The selection of reagents based upon the targeted nucleic acid is well known in the art as disclosed, for example, and without limitation, in the article cited earlier, "Padlock Probe Assay for Detection and Subtyping of Seasonal Influenza" by F. Neumann, et al. *Clinical Chemistry*, vol. 64, no. 12, pp. 1704-1712 (Dec. 1, 2018), where target-specific reagent components are selected in a padlock-probe-based method to identify influenza-positive samples. In an embodiment, for example, first target-specific set of reagent components 1815 are selected based upon a first target nucleic acid such that the first target-specific set of reagent components 1815 include the padlock probe target sequence appropriate to the first target nucleic acid. Likewise, in an embodiment, the second target-specific set of reagent components 1825 are selected based upon a second target nucleic acid (which can be different from the first target nucleic acid) such that the second target-specific set of reagent components 1825 include the padlock probe target sequence appropriate to the second target nucleic acid. Similarly, in an embodiment, third target-specific set of reagent components 1835 are selected based upon a third target nucleic acid (which can be different from both the first target nucleic acid and the second target nucleic acid) such that the third target-specific set of reagent components 1835 include the padlock probe target sequence appropriate to the third target nucleic acid. Further still, in an embodiment, fourth target-specific set of reagent components 1845 are selected based upon a fourth target nucleic acid (which can be different from the first, second, and third target nucleic acids) such that the fourth target-specific set of reagent components 1845 include the padlock probe target sequence appropriate to the fourth target nucleic acid.

FIG. 18 also depicts sample location 1880 and RCA-LAMP location 1850. In an embodiment, located on an electrode location 1805 in the RCA-LAMP location 1850 over the hydrophobic coating are RCA-LAMP reaction components 1855. Moreover, in an embodiment consistent with the present disclosure, RCA-LAMP reaction components 1855 are deposited at the RCA-LAMP location 1850 in a dried state. Consistent with the present disclosure, the RCA-LAMP components 1855 are "universal" reagents in the sense that the reagents in the RCA-LAMP components 1855 are selected to function with each of the first target-specific set of reagent components 1815, the second target-specific set of reagent components 1825, the third target-specific set of reagent components 1835, and the fourth target-specific set of reagent components 1845 regardless of the target nucleic acid each of the target-specific set of reagent components (1815, 1825, 1835, and 1845 in the present disclosure) are specifically selected to identify using the padlock probe technique. The "universal" reagents in the RCA-LAMP components 1855 include (where the reagents flagged with an asterisk, "*", are those that directly associate with the padlock probe backbone in the target-specific set of reagent components): ligase buffer; ligase enzyme*; RCA-LAMP buffer; TETRONIC; betaine; oligonucleotide strand displacement (OSD) probe*; deoxynucleotidetriphosphates (dNTPs); forward inside primer* (FIP); backward inside primer* (BIP); and Bst3* (polymerase with strand displacement activity).

Consistent with the present disclosure, the surface of DMF Board 1450 at sample location 1880 is accessible through both an opening in the spacer 1492 and the opening 1368 in top cover 1352. This allows a sample to be provided on the surface of DMF Board 1450 at sample location 1880 through the top of movable cartridge assembly 160. Likewise, consistent with the present disclosure, the dried RCA-LAMP reaction components 1855 on the surface of DMF Board 1450 at RCA-LAMP sample location 1850 is accessible through an opening in the spacer 1492 and the opening 1366 in top cover 1352. This allows fluid to be provided to the surface of DMF Board 1450 through the top of movable cartridge assembly 160 at RCA-LAMP location 1850, to hydrate any dried RCA-LAMP reaction components 1855. Also depicted in FIG. 18 is electrode connector 1801, which, consistent with an embodiment herein, can be connected to electrical "ground" through the DMF transport grid interface 165, and can also make contact with the spacer 1492 (which is conductive), and which, in turn, can make contact with a portion of the bottom of transparent plate 1490, where the hydrophobic coating has not been applied (through masking, for example) so that the conductive layer portion of transparent plate 1490 is thereby connected to electrical "ground."

Figure 19:
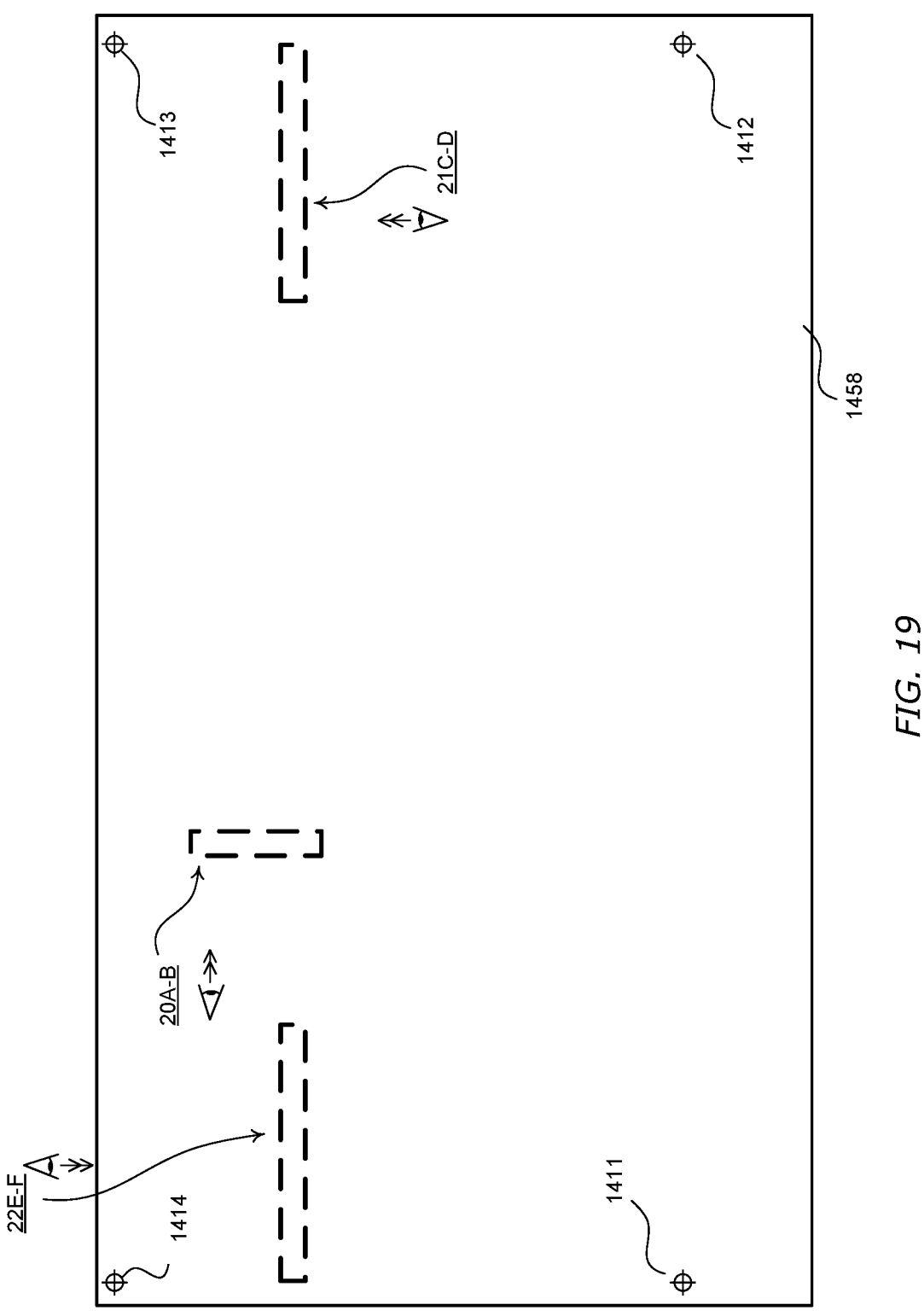

FIG. 19 depicts a top view of back frame 1458. Also shown in FIG. 19 are openings 1411, 1412, 1413, and 1414, discussed earlier in connection with FIG. 14. In a preferred embodiment, back frame 1458 can be composed of rigid material such as, but not limited to, FR-4 that (when secured to the top frame 1352 as described above) structurally maintains the relative order of the components of the movable cartridge assembly 160 and any necessary gaps between the components. In one embodiment, the entire structure of back frame 1458 lies within a rectangle that is approximately 100 mm×60 mm. In an embodiment, back frame 1458 can have a thickness of the order of millimeters (i.e., approximately 1 mm if relatively flat). In a preferred embodiment, where spacer 1492 is a conductor, back frame 1458 can generally be composed of non-conducting material.

Figures 20, 21:
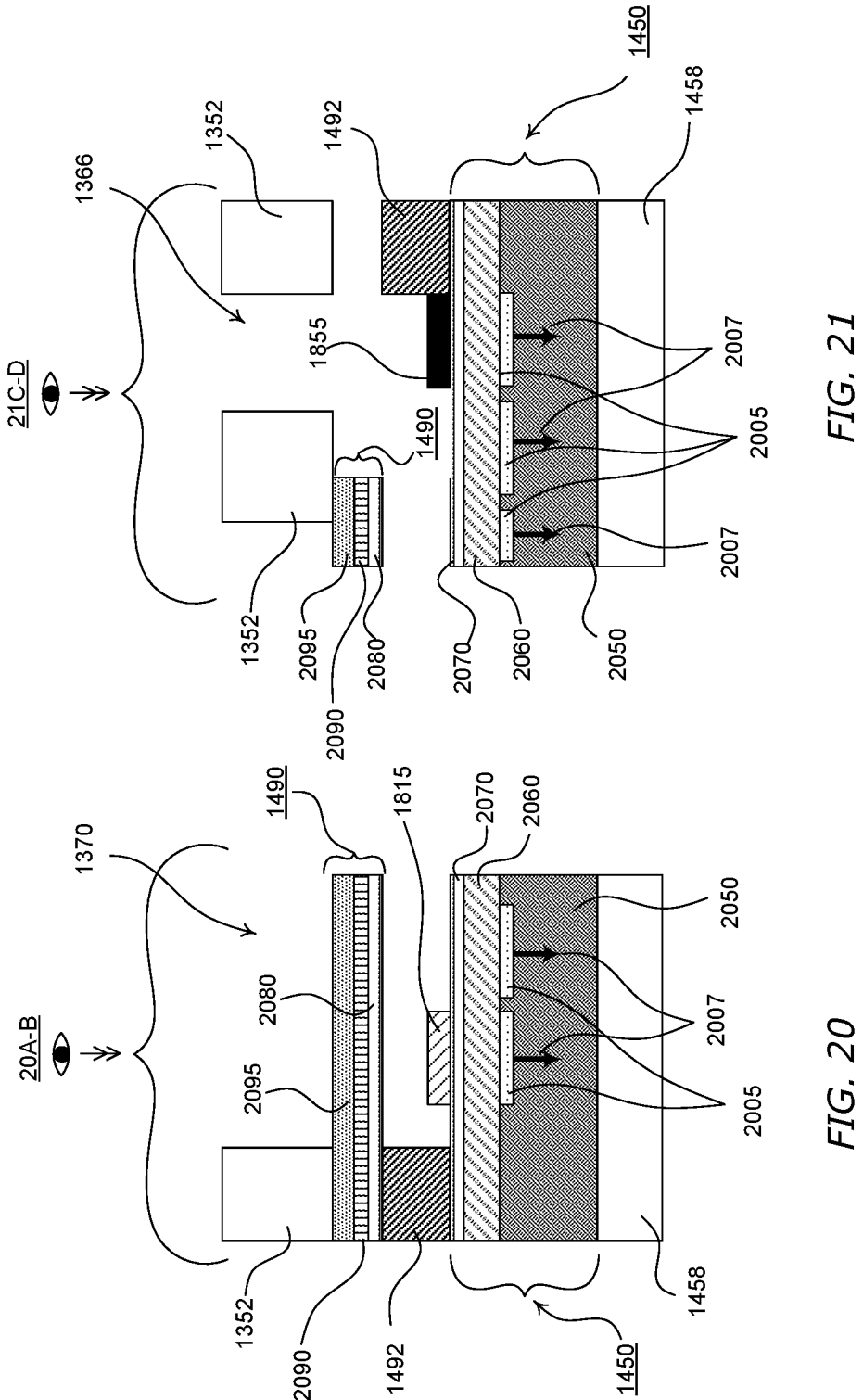
FIGS. 20-22 illustrate cross-section views of portions of the exemplary movable cartridge assembly of FIGS. 13 and 14.
Figure 22:
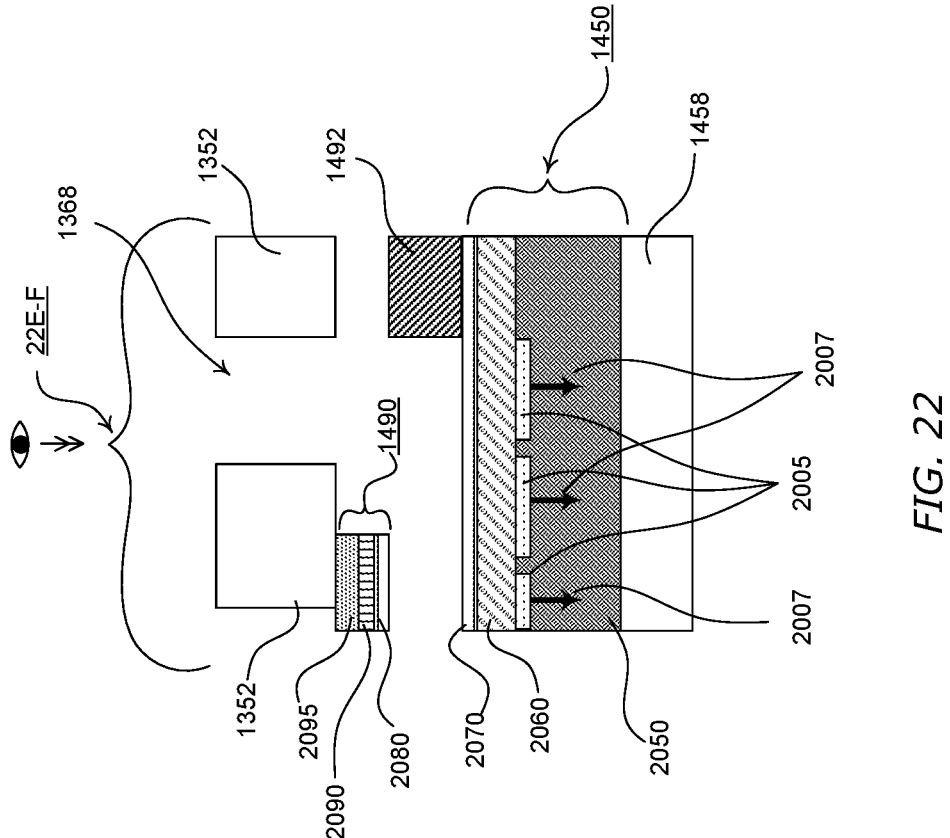

FIGS. 20-22 illustrate cross-section views of portions of the exemplary movable cartridge assembly of FIGS. 13 and 14.

FIG. 20 shows a cross-section view at location 20A-B, which includes a cross-section view of DMF Board 1450 within first target location 1810. Consequently, FIG. 20 includes a view of first target-specific set of reagent components 1815 on hydrophobic coating 2070. DMF Board 1450 further includes dielectric 2060, substrate 2050, electrodes 2005 and electrode connectors 2007 (where electrode connectors 2007, in turn, connect to the DMF transport grid interface 165 and are under control of DMF processor system 110). Spacer 1492 is shown, as well as transparent plate 1490, which can include glass layer 2095, conductive layer 2090, and hydrophobic coating 2080. Dielectric 2060 can include material such as, but not limited to, parylene-C and can be formed in a layer with a thickness from approximately 2-20 microns.

FIG. 21 shows a cross-section view at location 21C-D, which includes a cross-section view of DMF Board 1450 within RCA-LAMP location 1850. Consequently, FIG. 21 includes a view of RCA-LAMP reaction components 1855 on hydrophobic coating 2070. As in FIG. 20, DMF Board 1450 further includes dielectric 2060, substrate 2050, electrodes 2005 and electrode connectors 2007 (where electrode connectors 2007, in turn, connect to the DMF transport grid interface 165, and are under control of DMF processor system 110). Spacer 1492 is shown, as well as transparent plate 1490, which includes glass layer 2095, conductive layer 2090, and hydrophobic coating 2080.

FIG. 22 shows a cross-section view at location 22E-F, which includes a cross-section view of DMF Board 1450 within sample location 1880. As in FIGS. 20 and 21, DMF Board 1450 further includes dielectric 2060, substrate 2050, electrodes 2005 and electrode connectors 2007 (where electrode connectors 2007, in turn, connect to the DMF transport grid interface 165, and are under control of DMF processor system 110). Spacer 1492 is shown, as well as transparent plate 1490, which includes glass layer 2095, conductive layer 2090, and hydrophobic coating 2080.

Figure 23:
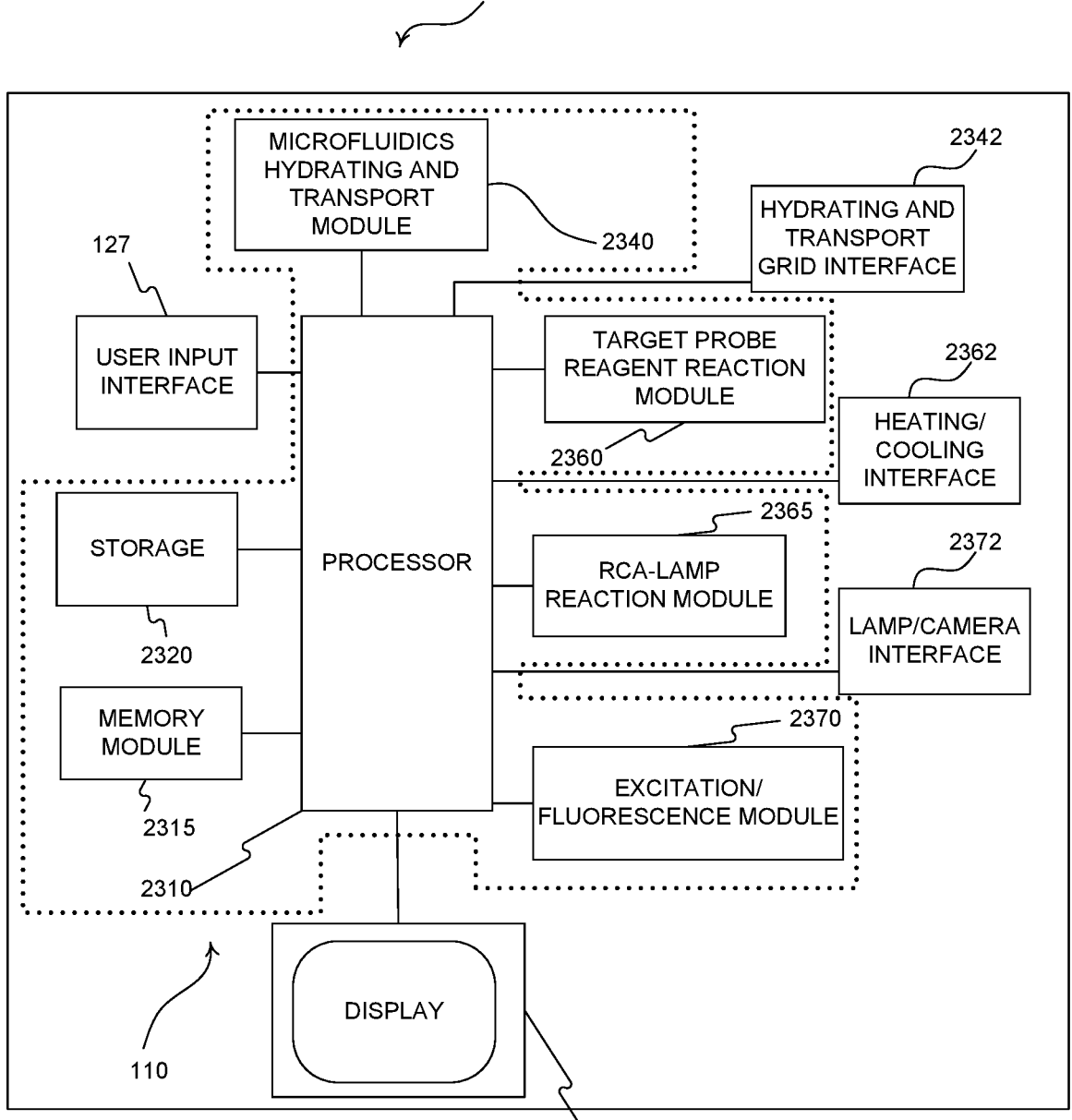
FIG. 23 is a schematic of an exemplary data processing system for the mixing and evaluation of samples consistent with the present disclosure.

FIG. 23 is a schematic diagram of a data processing system 2300 for managing the mixing and evaluating of samples. The system 2300 can include a processor 2310, a memory module 2315, a storage device 2320, an input interface 127, a display device 125, a microfluidics hydrating and transport module 2340, a target probe reagent reaction module 2360, an RCA-LAMP reaction module 2365, and an excitation/fluorescence module 2370. System 2300 can also include a hydrating and transport grid interface 2342, a heating/cooling interface 2362, and a lamp/camera interface 2372. The system 2300 can include additional, fewer, and/or different components than those listed above. The type and number of listed devices are exemplary only and not intended to be limiting.

The processor 2310 can be a central processing unit ("CPU") or a graphic processing unit ("GPU"). The processor 2310 can execute sequences of computer program instructions to perform various processes that will be explained in greater detail below. The memory module 2315 can include, among other things, a random access memory ("RAM") and a read-only memory ("ROM"). Generally, memory module 2315 can be a non-transitory computer readable medium. The computer program instructions can be accessed and read from the ROM, or any other suitable memory location, and loaded into the RAM for execution by the processor 2310. The processor 2310 can include one or more printed circuit boards, and/or a microprocessor chip.

The storage device 2320 can include any type of mass storage suitable for storing information. For example, the storage device 2320 can include one or more hard disk devices, optical disk devices, or any other storage devices that provide data storage space. For example, the storage device 2320 can store data related to a data processing process, such as the processing of data received from the camera system 180, and any intermediate data created during the data processing process. The storage device 2320 can also include analysis and organization tools for analyzing and organizing data and/or information contained therein.

In an embodiment, the hydrating and transport grid interface 2342 is configured to provide the electrical impulses (or the instructions for impulses) to the DMF Board 450, the DMF Board 1450, transparent plate 490, and transparent plate 1490 (as appropriate) to cause microfluidic flow to occur in the gap between the surface of DMF Board 450 and the bottom of transparent plate 490, or between the surface of DMF Board 1450 and the bottom of transparent plate 1490 (as appropriate). In another embodiment, the hydrating and transport grid interface 2342 can be configured for two-way communication between the DMF Board 450, the DMF Board 1450, the device 100, and the system 2300. For example, consistent with one embodiment, the hydrating and transport grid interface 2342 can be configured to receive data from the DMF Board 450 (or the DMF Board 1450) and/or device 100 and store the data into the storage device 2320. As described above, the hydrating and transport grid interface 2342 can be further configured to send control instructions to the DMF Board 450 (or to the DMF Board 1450) to initiate and terminate movement of fluid aliquots over the DMF Board 450 (or the DMF Board 1450). The hydrating and transport grid interface 2342 can be further configured to send control instructions to the DMF Board 450 (or the DMF Board 1450) and/or device 100 initiate and terminate hydration operations. For example, device 100 may include a fluid reservoir (not shown) coupled to the hydrating and transport grid interface 2342, where the fluid reservoir is configured to provide fluid to RCA-LAMP location 850 (or RCA-LAMP location 1850) upon the receipt of control instructions from the hydrating and transport grid interface 2342. In an embodiment the digital microfluidics hydrating and transport module 2340 can be configured to manage data and processing instructions associated with the transport of fluid aliquots over the DMF Board 450, the DMF Board 1450, and associated with hydrating dried components that may be deposited or printed on the DMF Board 450 and the DMF Board 1450. Software consistent with one embodiment of the current disclosure for controlling microfluidic flow in the gap between the surface of DMF Board 450 and the bottom of transparent plate 490, or between the surface of DMF Board 1450 and the bottom of transparent plate 1490 (as appropriate), as well as portions of hardware consistent with one embodiment of the current disclosure, is available under the platform name OPEN-DROP from GAUDILABS at: https://gaudishop.ch/index-.php/product/opendrop-v4-digital-microfluidics-platform/.

In an embodiment, the heating/cooling interface 2362 can also be configured for two-way communication between the DMF Board 450, the DMF Board 1450, the heating/cooling device 190, and the system 2300. Consistent with one embodiment, the heating/cooling interface 2362 can be configured to receive data from the DMF Board 450 (or the DMF Board 1450) (or sensors adjacent to DMF Board 450 and/or DMF Board 1450) and/or the heating/cooling device 190 and store the data into the storage device 2320. The heating/cooling interface 2362 can be further configured to send control instructions to the heating/cooling device 190 to initiate and terminate heating and cooling operations.

In an embodiment the target probe reagent reaction module 2360 can be configured to manage data and processing instructions associated with the annealing and ligation of target-specific set of reagent components and aliquots of a sample. Further still, in an embodiment, the RCA-LAMP reaction module 2365 can be configured to manage data and processing instructions associated with the RCA-LAMP process at the target locations.

Consistent with the present disclosure, the lamp/camera interface 2372 can be configured for two-way communication between the camera system 180 and the system 2300. Consistent with one embodiment, the lamp/camera interface 2372 can be configured to receive data from the camera system 180 and store the data into the storage device 2320. The lamp/camera interface 2372 can be further configured to send control instructions to lamp 170 and camera system 180 to initiate and terminate excitation radiation and to initiate and stop camera operations for monitoring fluorescence.

In an embodiment the excitation/fluorescence module 2370 can be configured to manage data and processing instructions associated with the provision of excitation radiation and the monitoring of fluorescence from the target locations.

The system 2300 can be accessed and controlled by a user using the input interface 127. The input interface 127 can be available for the user to input information into data processing system 2300, and can include, for example, a keyboard, a mouse, a touch screen and/or optical or wireless computer input devices. The user can input control instructions via the input interface 127 to control the operation of the DMF processing system 110, the heating/cooling device 190, the lamp 170, and/or the camera system 180.

The system 2300 can also provide visualized information to the user via the display 125. For example, the display 125 can include a computer screen and make available a graphical user interface ("GUI") to the user. The display 125 can display an image of the target locations on DMF Board 450 (or DMF Board 1450) during an RCA-LAMP process. Consistent with another embodiment, the display 125 can also display an abbreviated inspection report, or a simple indicator, to the user indicating certain characteristics of biological items identified in a provided sample.

Figure 24:
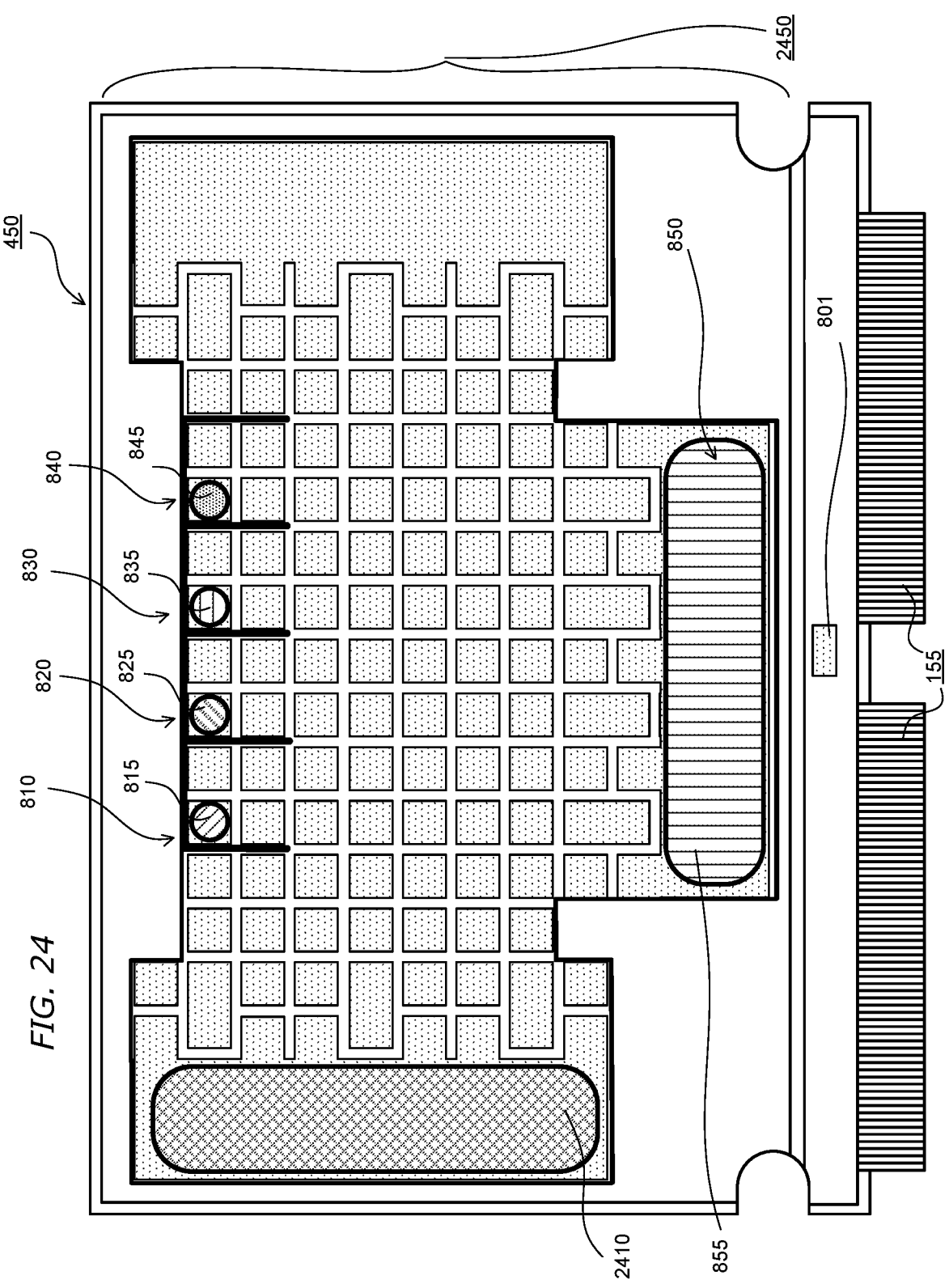
FIG. 24 illustrates a top view of a DMF Board consistent with the exemplary movable cartridge assembly of FIGS. 3 and 4 with a provided sample.

FIG. 24 illustrates a top view of DMF Board 450 consistent with exemplary operation of device 100 with movable cartridge assembly 150. (Although the description of operation of device 100 with movable cartridge assembly 150 is provided below with FIGS. 24-33, one of ordinary skill in the art should immediately understand and appreciate the operation of device 100 with movable cartridge assembly 160.)

FIG. 24 illustrates the view of DMF Board 450 previously provided in FIG. 8. However, in FIG. 24, sample 2410 has been introduced to the surface 2450 of DMF Board 450. Consistent with the present disclosure, as described above, sample 2410 may be introduced to the surface 2450 of DMF Board 450 from the top of movable cartridge assembly 150 through opening 368.

Consistent with the present disclosure, sample 2410 is a liquid. In one embodiment, sample 2410 can include an addition of between 5 and 20%, by volume, of a hydrophobic oil, immiscible with water, such as polydimethyl siloxane (PDMS), or a similar fluid. One of ordinary skill in the art would appreciate that the addition of between 5 and 20%, by volume, of such a hydrophobic oil can minimize evaporation of sample droplet during heating.

Figure 25:
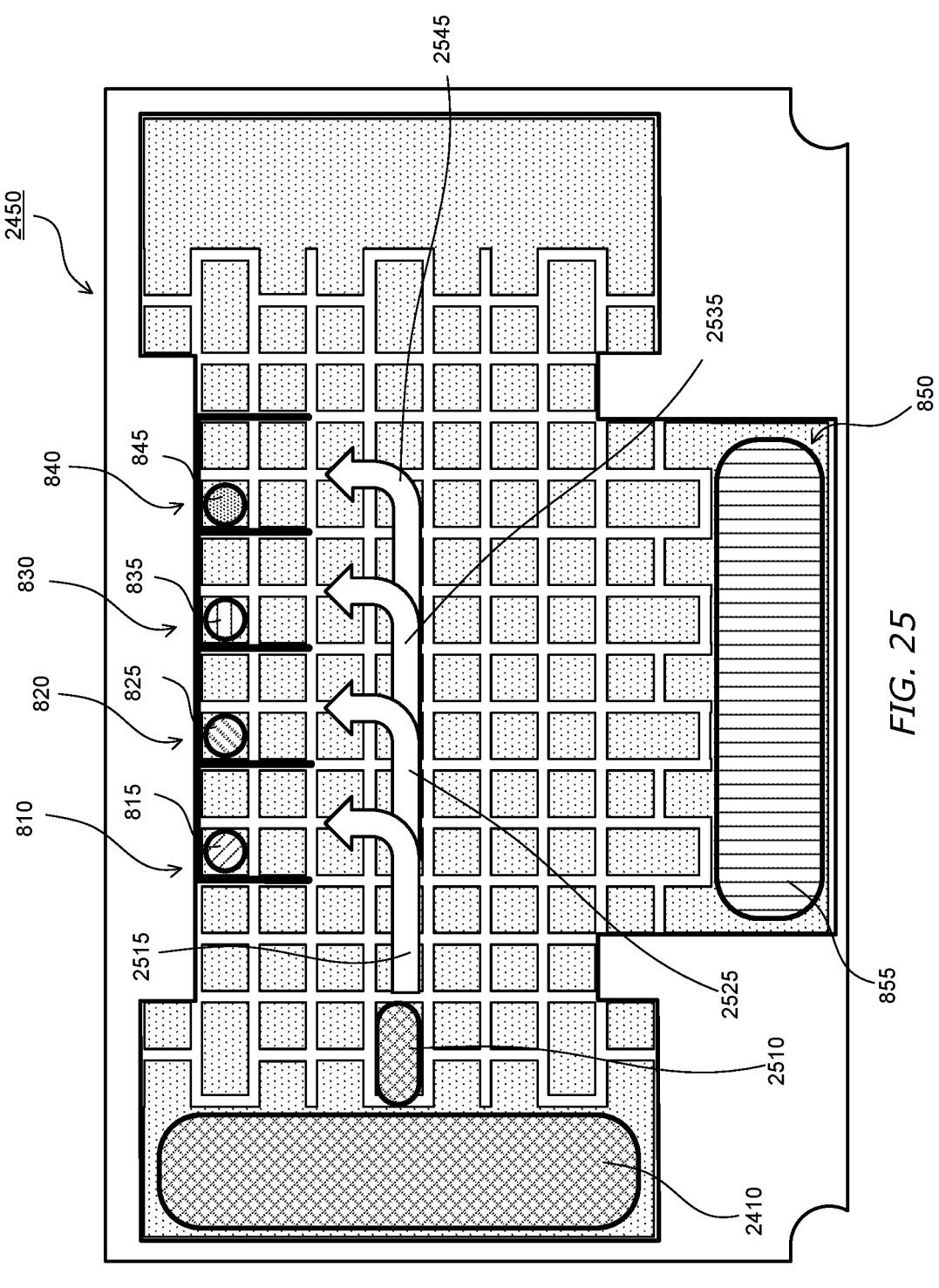
FIG. 25 illustrates a top view of a surface of a DMF Board consistent with the exemplary movable cartridge assembly of FIGS. 3 and 4, depicting movement of sample aliquots.

FIG. 25 illustrates a view of surface 2450, and depicts how a single aliquot (or series of aliquots) of sample 2410 can be transported across surface 2450 using digital microfluidics to arrive at target locations. For example, arrow 2515 depicts a possible route of aliquot 2510 to first target location 810; arrow 2525 depicts a possible route of aliquot 2510 to second target location 820; arrow 2535 depicts a possible route of aliquot 2510 to third target location 830; and arrow 2545 depicts a possible route of aliquot 2510 to fourth target location 840.

Figure 26:
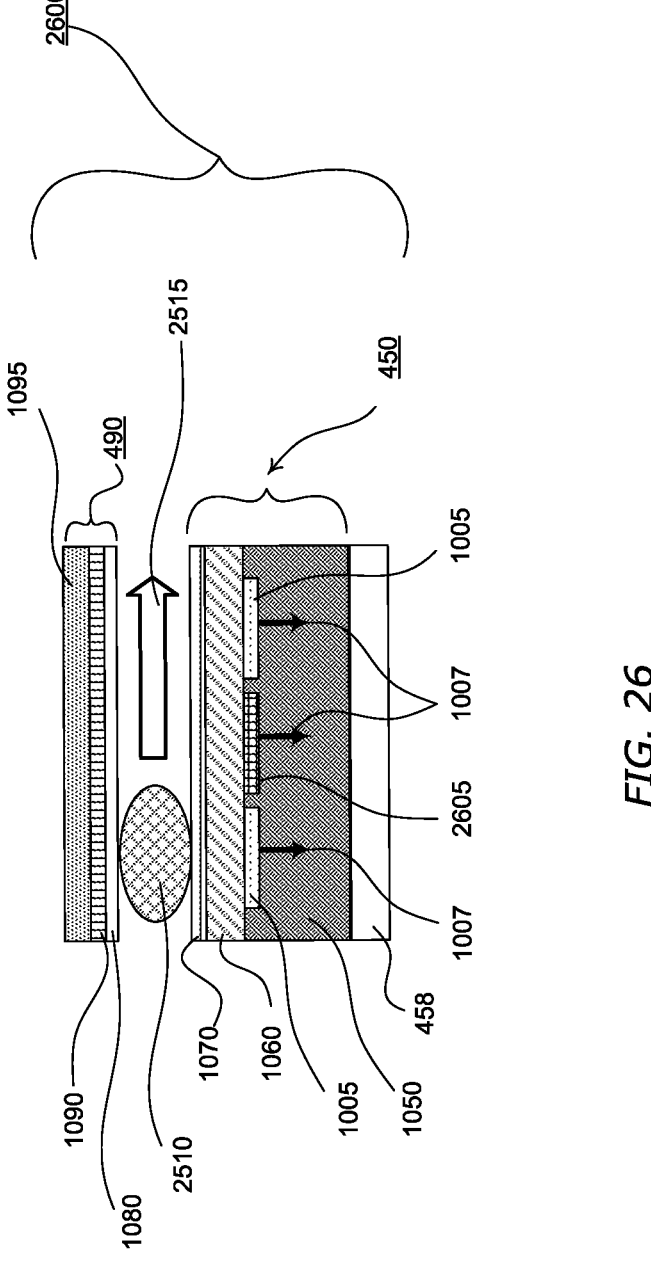
FIG. 26 illustrates a cross section view of a portion of the digital microfluidics system consistent with the exemplary movable cartridge assembly of FIGS. 3 and 4, depicting movement of a sample aliquot.

FIG. 26 provides a cross section view of digital microfluidics system 2600, and depicts the movement of aliquot 2510 according to arrow 2515. As shown in FIG. 26, electrode 1005 is not provided with an electrical charge (relative to electrical "ground"). Electrode 2605, however, is provided with a charge through its associated electrode connector 1007. The presence of the electrical charge on electrode 2605 causes aliquot 2510 to move in the direction of electrode 2605. Consistent with DMF processing systems, after aliquot 2510 is over electrode 2605, then that electrode can be returned to "ground," and the next subsequent electrode in the direction of arrow 2515 is provided a charge relative to "ground." In this way, aliquot 2510 is transported across surface 2450 of FIG. 25.

Figures 27, 28:
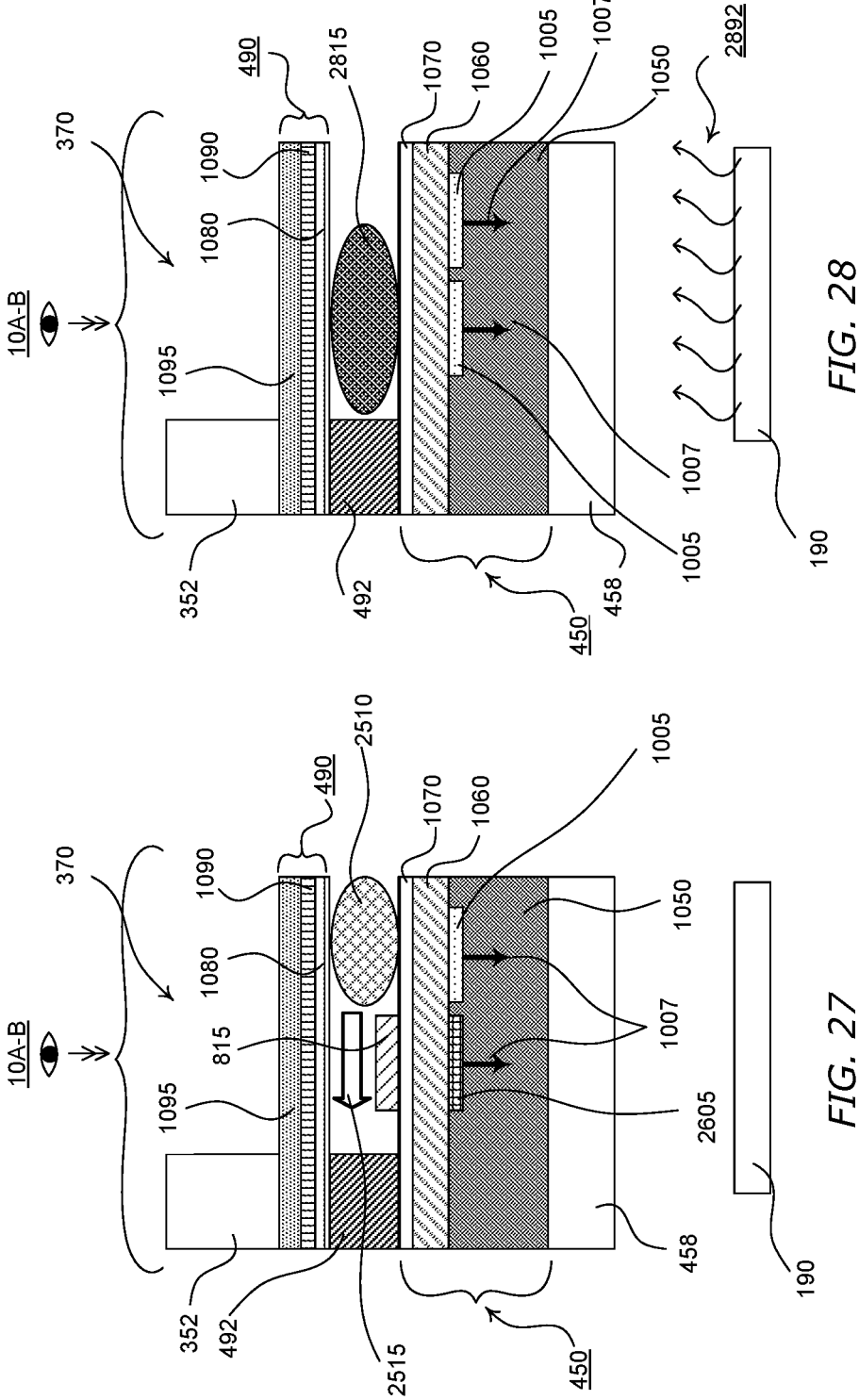
FIGS. 27-28 illustrate cross section views of portions of the exemplary movable cartridge assembly of FIGS. 3 and 4, depicting movement, mixing, and heating of aliquots.

FIG. 27 shows a cross-section view at location 10A-B, which includes a cross-section view of DMF Board 450 within first target location 810, and also shows aliquot 2510 being transported over first target-specific set of reagent components 815 on hydrophobic coating 1070. As has been shown previously, DMF Board 450 further includes dielectric 1060, substrate 1050, electrode 1005 and electrode connectors 1007 (where electrode connectors 1007, in turn, connect to the DMF transport grid interface 155, and are under control of DMF processor system 110). Spacer 492 is shown, as well as transparent plate 490, which includes glass layer 1095, conductive layer 1090, and hydrophobic coating 1080. Furthermore, heating/cooling device 190 is shown as being located beneath first target location 810.

As shown in FIG. 27, consistent with the present disclosure, electrode 1005 is not provided with an electrical charge (relative to electrical "ground"). Electrode 2605, however, is provided with a charge through its associated electrode connector 1007. The presence of the electrical charge on electrode 2605 causes aliquot 2510 to move in the direction of electrode 2605 over first target-specific set of reagent components 815 on hydrophobic coating 1070. In this way, when aliquot 2510 is over electrode 2605, then that electrode can be returned to "ground" (which is depicted in FIG. 28), and aliquot 2510 from FIG. 27 mixes with first target-specific set of reagent components 815 from FIG. 27 to form first mixture 2815, depicted in FIG. 28.

Consistent with the present disclosure, and as depicted in FIGS. 27 and 28, the aliquot 2510 of sample 2410 has been transported onto a pre-designated electrode located in the first target location 810, where the first target-specific set of reagent components 815 have been deposited or printed (which include a target-specific padlock probe, a ligation enzyme, and buffer components necessary for a ligation reaction to proceed).

Once aliquot 2510 reaches the first target location 810, aliquot 2510 will absorb the deposited (or printed) reagents 815 so that they become part of the liquid sample 2815.

Consistent with the present disclosure, heating/cooling device 190 provides heat 2892 to first mixture 2815 until first mixture 2815 reaches a temperature of approximately 95 degrees Celsius. This allows the padlock probe to access the nucleic acid sequence of the sample 2410. The first mixture 2815 is then cooled (or allowed to cool), and if the nucleic acid sequence of the sample matches the target-specific complementary sequences of the padlock probe, the padlock probe will form a circular confirmation. The ligase then covalently connects the two padlock probe target-specific arms so that the circular confirmation becomes permanent. Consistent with the present disclosure, if the sample 2410 does not contain the target genetic material, ligation of the padlock probe does not occur.

Figure 29:
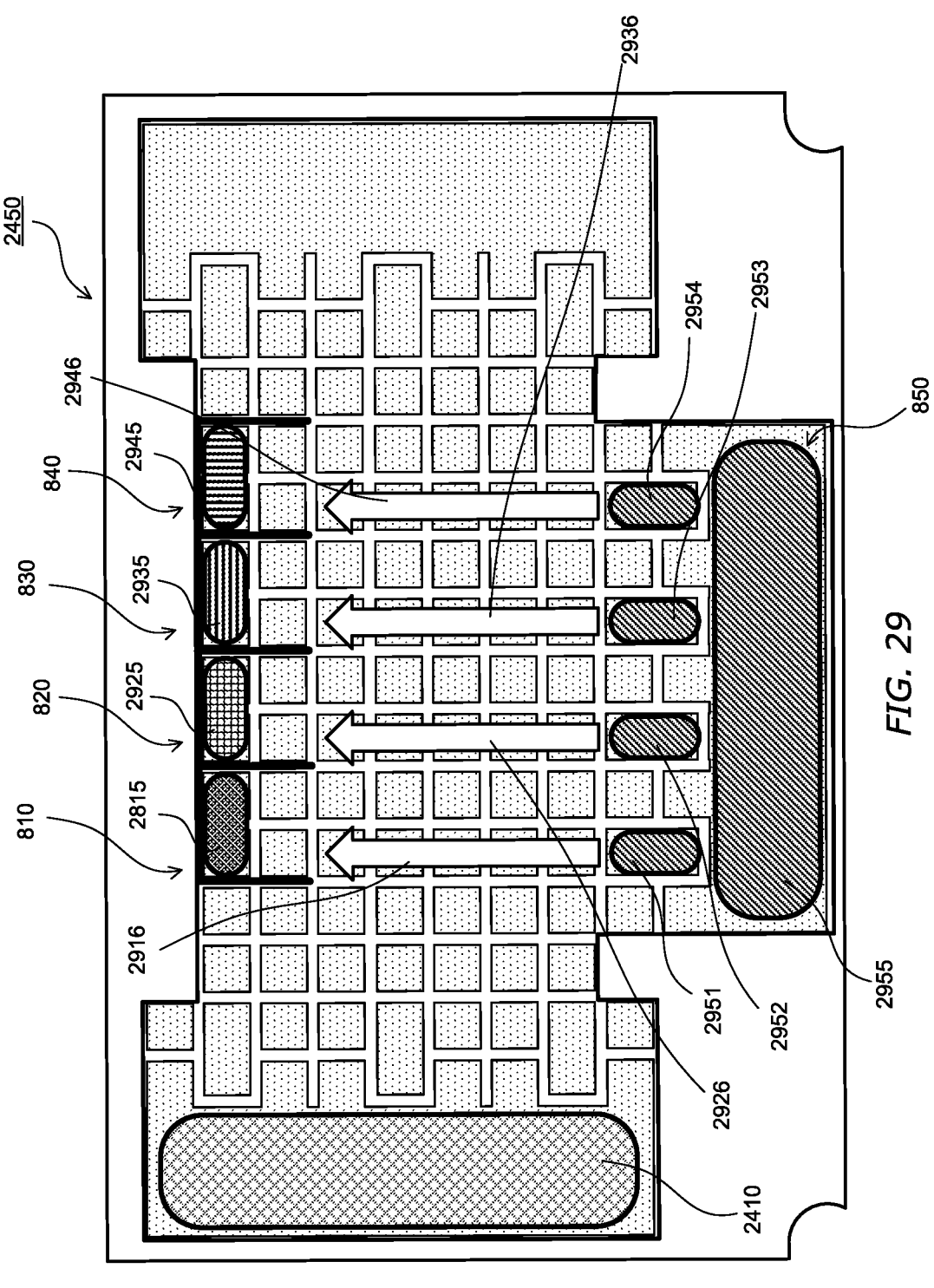
FIG. 29 illustrates a top view of a surface of a DMF Board consistent with the exemplary movable cartridge assembly of FIGS. 3 and 4, depicting movement of aliquots of hydrated RCA-LAMP components.

FIG. 29 illustrates a view of surface 2450, and depicts how a single aliquot 2951 (or series of aliquots 2952, 2953, and/or 2954) of hydrated RCA-LAMP Reaction Components 2955 can be transported across surface 2450 using digital microfluidics to arrive at target locations. For example, arrow 2916 depicts a possible route of first aliquot 2951 to first target location 810; arrow 2926 depicts a possible route of aliquot 2952 to second target location 820; arrow 2936 depicts a possible route of aliquot 2953 to third target location 830; and arrow 2946 depicts a possible route of aliquot 2954 to fourth target location 840. Consistent with the present disclosure, first aliquot 2951, second aliquot 2952, third aliquot 2953, and fourth aliquot 2954 can consist of less than 10 microliters of hydrated RCA-LAMP Reaction Components 2955.

Further still, consistent with the present disclosure, if RCA-LAMP Reaction Components 855 are deposited in a dried form, then RCA-LAMP Reaction Components 855 can be hydrated prior to the operation depicted in FIG. 29 through the introduction of fluid introduced to the surface 2450 of DMF Board 450 at RCA-LAMP location 850. Consistent with the present disclosure, as described above, fluid may be introduced to the surface 2450 of DMF Board 450 at RCA-LAMP location 850 from the top of movable cartridge assembly 150 through opening 366. Such fluid for purposes of hydrating the RCA-LAMP components 855 can be introduced when sample 2410 is introduced, or later. Moreover, device 100 may include a fluid reservoir coupled to and under control of microfluidics hydrating and transport module 2340 for just this purpose.

After first aliquot 2951, second aliquot 2952, third aliquot 2953, and fourth aliquot 2954 have been transported to first target location 810, second target location 820, third target location 830, and fourth target location 840 (respectively) using digital microfluidics system 2600, each of the aliquots mixes with the fluid already present in each of the target locations. As shown in FIG. 29, these previously present mixtures include first mixture, 2815, second mixture 2925, third mixture 2935, and fourth mixture 2945.

Consistent with the present disclosure, the fluid mixtures in each of the target locations is heated again, but only to approximately 65 degrees Celsius. These mixtures include: a mixture of first aliquot 2951 and first mixture 2815 at first target location 810—which becomes first mixture 3015 depicted in FIG. 30; a mixture of second aliquot 2952 and second mixture 2925 at second target location 820—which becomes second mixture 3025 depicted in FIG. 30; a mixture of third aliquot 2953 and third mixture 2935 at third target location 830—which becomes third mixture 3035 depicted in FIG. 30; and a mixture of fourth aliquot 2954 and fourth mixture 2945 at fourth target location 840—which becomes fourth mixture 3045 depicted in FIG. 30. At this temperature, the LAMP primers specific to the padlock probe backbone (which are common for all target-specific padlock probes) and polymerase bind to the ligated padlock probe and begin the LAMP reaction. As the reaction progresses, an oligonucleotide strand displacement (OSD) probe binds to a loop region of the LAMP products. This causes the OSD quencher to be removed from the probe, which allows for unquenched fluorescence from the fluorophore attached to the OSD probe. As more LAMP amplification occurs, more LAMP loop products are made, and more OSD probes bind and create more fluorescence.

Figure 30:
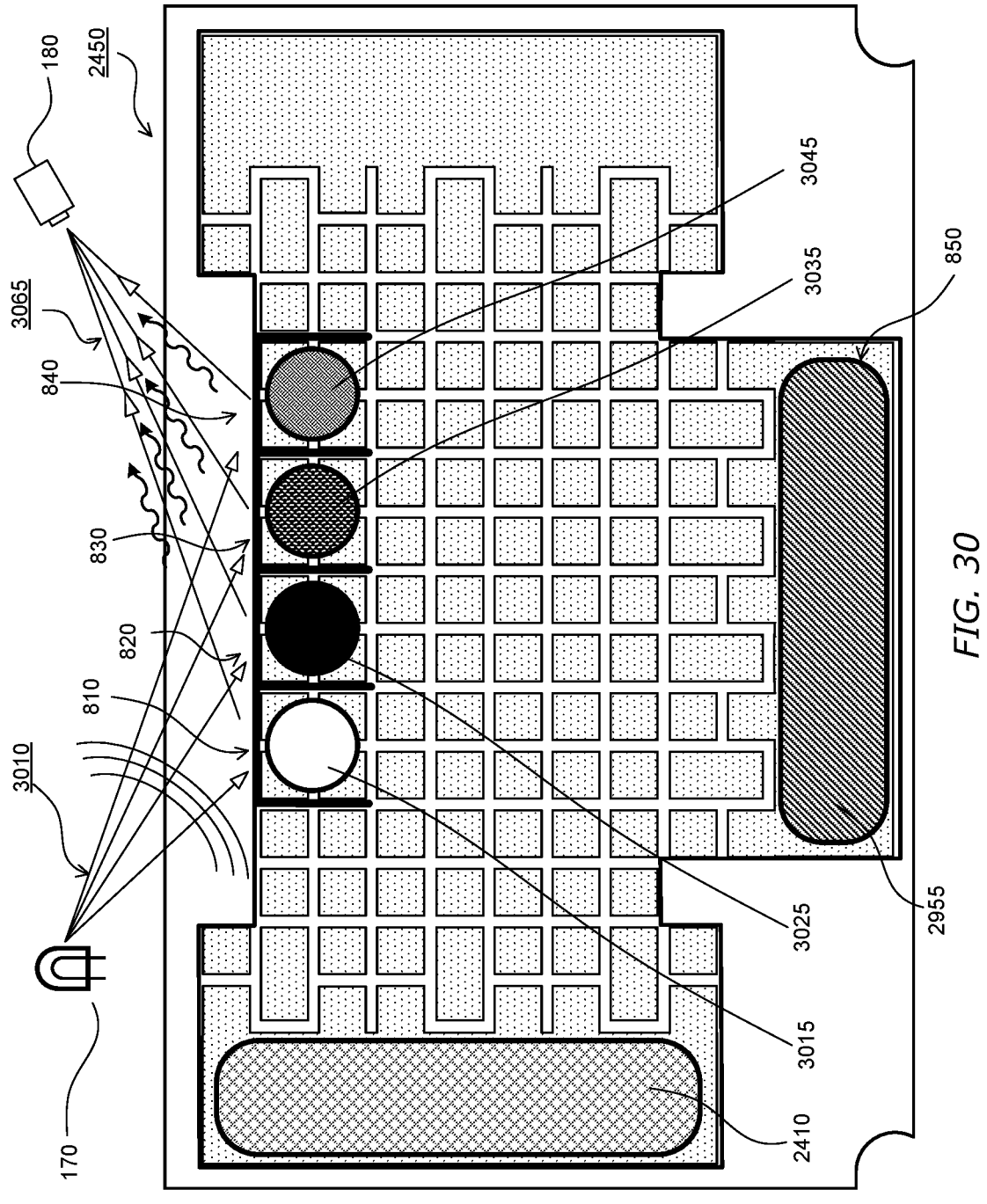
FIG. 30 illustrates a top view of a surface of a DMF Board consistent with the exemplary movable cartridge assembly of FIGS. 3 and 4, depicting mixtures on the surface of the DMF Board, excitation radiation, and possible fluorescence.

FIG. 30 illustrates a view of surface 2450, and depicts how final mixtures 3015, 3025, 3035, and 3045 at the target locations 810, 820, 830, and 840 (respectively) may be irradiated by excitation radiation 3010 from lamp 170 to determine if fluorescence 3065 is produced. The fluorescence of the mixtures in FIG. 30 can be monitored in real-time with camera system 180, where camera system 180 can include an appropriate filter. Again, if the sample 2410 does not contain the target genetic material, ligation of the padlock probe does not occur. Thus, the LAMP reaction cannot commence in the absence of ligated padlock probe, and samples 2410 without target genetic material cannot fluoresce.

FIG. 31 shows a cross-section view at location 10A-B, which includes a cross-section view of DMF Board 450 within first target location 810, and also shows first aliquot 2951 being transported to mix with first mixture 2815 on hydrophobic coating 1070. As has been shown previously, DMF Board 450 further includes dielectric 1060, substrate 1050, electrode 1005 and electrode connectors 1007 (where electrode connectors 1007, in turn, connect to the DMF transport grid interface 155, and are under control of DMF processor system 110). Spacer 492 is shown, as well as transparent plate 490, which includes glass layer 1095, conductive layer 1090, and hydrophobic coating 1080. Furthermore, heating/cooling device 190 is shown as being located beneath first target location 810.

As shown in FIG. 31, consistent with the present disclosure, electrode 1005 is not provided with an electrical charge (relative to electrical "ground"). Electrode 2605, however, is provided with a charge through its associated electrode connector 1007. The presence of the electrical charge on electrode 2605 causes aliquot 2951 to move in the direction of electrode 2605 to mix with first mixture 2815. In this way, when aliquot 2951 is over electrode 2605, then that electrode can be returned to "ground" (which is depicted in FIG. 28), and aliquot 2951 from FIG. 30 mixes with first mixture 2815 from FIG. 30 to form first mixture 3015, depicted in FIG. 32.

Consistent with the present disclosure, and as depicted in FIGS. 31 and 32, heating/cooling device 190 provides heat 3292 to first mixture 3015 until first mixture 3015 reaches a temperature of approximately 65 degrees Celsius. FIG. 32 also depicts a perspective associated with view 33A, shown in FIG. 33.

FIG. 33 illustrates a cross section view of a portion of DMF Board 450, and depicts how first mixture 3015 at the first target location 810 may be irradiated by excitation radiation 3010 from lamp 170 to determine if fluorescence 3065 is produced.

Consistent with the current disclosure, a single sample 2410 can be analyzed for different targets through spatial multiplexing where a different padlock probe is located at each of the first target location 810, the second target location 820, the third target location 830, and the fourth target location 840. Similarly, different samples can be independently analyzed (for the same or different targets) at different locations on the same platform. One of ordinary skill in the art would appreciate that movable cartridge assembly 160, for example, provides reservoir locations in addition to sample location 1880 and RCA-LAMP location 1850, that can accommodate additional samples. This spatial multiplexing is enabled through sample and reactant transport via digital microfluidics. The sequence-specific probe described above, which results in fluorescence, is one method of LAMP detection consistent with the current disclosure. In another embodiment consistent with the current disclosure, bivalent metal ions, such as magnesium, calcium or manganese, can be added so that they are present when the final mixtures (3015, 3025, 3035, and 3045) are formed. In this alternative embodiment, these ions can form complexes with a LAMP byproduct (pyrophosphate), which will precipitate as LAMP proceeds. This turbidity of the precipitate can be measured, or observed, to determine whether a LAMP reaction has occurred, thereby confirming identification of a target nucleic acid. Further still, in another embodiment, methods of LAMP detection can include the use of DNA-intercalating dyes such as SYBR Green, EvaGreen, SYBR Gold, SYBR Safe, berberine, etc.

Consistent with the current disclosure, in an embodiment, the padlock probe backbone can include: 1) a sequence-specific probe binding site; 2) a B1 primer binding site, a B2 primer binding site; 3) a complement sequence to an F1 primer binding site, a complement sequence to an F2 primer binding site, and a complement sequence to a loop primer binding site.

FIGS. 34 and 35 depict flowcharts consistent with methods for nucleic acid identification of material in a sample disclosed herein.

FIGS. 34 and 35 include a step 3405 of providing a microfluidics system with a movable cartridge assembly. Consistent with the current disclosure, such a microfluidics system can include digital microfluidics system 2600 with movable cartridge assembly 150 and/or movable cartridge assembly 160. FIGS. 34 and 35 next depict dispensing a sample onto a movable cartridge assembly (step 3410), followed by transporting an aliquot of the sample received on the surface to the target location (step 3415 and/or step 3515). Consistent with the present disclosure, FIGS. 34 and 35 next depict the step of mixing an aliquot of the sample (for example, sample 2410) and a first target-specific set of reagent components (for example, components 815) at a first target location (step 3420 and/or step 3520). After an aliquot of the sample is mixed with the first target-specific set of reagent components at the first target location (for example, first target location 810), FIGS. 34 and 35 depict the step of annealing and ligation of the first target-specific set of reagent components mixed with the aliquot of the sample by heating the mixture to approximately 95 degrees Celsius followed by cooling (step 3445 and/or step 3545).

Consistent with the present disclosure, the methods of FIGS. 34 and 35 can also include the step of hydrating RCA-LAMP reaction components on the movable cartridge assembly (step 3450). One of ordinary skill in the art would appreciate the step 3450 does not have to follow step 3445 (or step 3545), but can occur earlier, such as before step 3410.

Consistent with the present disclosure, the methods of FIGS. 34 and 35 include the step of transporting an aliquot of hydrated RCA-LAMP reaction components on the movable cartridge assembly to the first target location (step 3455 and/or step 3555). Step 3460 (and/or step 3560) includes mixing the aliquot of hydrated RCA-LAMP reaction components with the mixture present at the first target location—previously provided by step 3445 (and/or step 3545).

Step 3485 (and/or step 3585), consistent with the present disclosure provides for heating the fluid at the first target location to approximately 65 degrees Celsius.

An embodiment may also include providing excitation radiation to the first target location (step 3490 and/or step 3590), and monitoring fluorescence from the first target location (step 3495 and/or step 3595).

Consistent with a further embodiment, FIG. 35 includes a further step of transporting a second aliquot of the sample received on the surface to a second target location (step 3525). FIG. 35 further depicts the step of mixing the second aliquot of the sample (for example, sample 2410) and a second target-specific set of reagent components (for example, components 825) at a second target location (step 3530). After the aliquots of the sample are mixed with their respective target-specific set of reagent components at their respective locations, FIG. 35 depicts the step of annealing and ligation of the first target-specific set of reagent components mixed with the first aliquot of the sample and annealing and ligation of the second target-specific set of reagent components mixed with the first second of the sample by heating each mixture to approximately 95 degrees Celsius followed by cooling (step 3545).

Consistent with the present disclosure, the method of FIG. 35 can also include the step of hydrating RCA-LAMP reaction components on the movable cartridge assembly (step 3450). One of ordinary skill in the art would appreciate the step 3450 does not have to follow step 3545, but can occur earlier, such as before step 3410.

Consistent with the present disclosure, the method of FIG. 35 includes the further step of transporting a second aliquot of hydrated RCA-LAMP reaction components on the movable cartridge assembly to the second target location (step 3565). Step 3570 includes mixing the second aliquot of hydrated RCA-LAMP reaction components with the mixture present at the second target location—previously provided by step 3545.

Step 3585, consistent with the present disclosure provides for heating the fluid at the second target location to approximately 65 degrees Celsius.

An embodiment may also include providing excitation radiation to the first target location (step 3590), and monitoring fluorescence from the second target location (step 3596).

One of ordinary skill in the art would appreciate that the embodiments disclosed herein can be used in many settings to identify biological targets using any sample type (once purified) including, but not limited to: POC diagnostics, population screening, emergency response situations, bio/chemical defense, food testing, environmental testing, and biological testing in zero-gravity settings.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. While certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems, methods, and non-transitory computer readable media falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A device for nucleic acid identification of material in a sample, the device comprising:
    a microfluidics system; and
    a heat source;
    the microfluidics system comprising a movable cartridge assembly;
    the movable cartridge assembly comprising:
        a surface configured to receive the sample;
        at least one target-specific set of reagent components deposited on the surface at a target location;
        at least a second target-specific set of reagent components deposited on the surface at a second target location;
        at least one set of RCA-LAMP reaction components deposited on the surface at an RCA-LAMP location;
        the at least one target-specific set of reagent components including:
            at least one target-specific padlock probe reagent component;
            at least one target probe-associated ligase enzyme component; and
            at least one target probe-associated set of ligase buffer components;
        the second target-specific set of reagent components including:
            a second target-specific padlock probe reagent component;
            the at least one target probe-associated ligase enzyme component; and
            the at least one target probe-associated set of ligase buffer components; and
        the at least one set of RCA-LAMP reaction components including:
            at least one polymerase buffer component;
            at least one polymerase enzyme with strand displacement activity;
            a betaine additive;
            a poloxamine surfactant additive;
            a sequence-specific probe;
            dNTPs; and
            a primer mix;
        the primer mix including:
            a forward inside primer specific to a backbone of the at least one target-specific padlock probe reagent component; and
            a backward inside primer specific to the backbone of the at least one target-specific padlock probe reagent component;
        wherein the second target-specific padlock probe reagent component includes the backbone of the at least one target-specific padlock probe reagent component.

2. The device of claim 1,
    wherein the ligase enzyme component is a Taq DNA ligase enzyme component; and
    wherein the set of ligase buffer components are a set of Taq DNA ligase buffer components.

3. The device of claim 1,
    wherein the ligase enzyme component is a RNA ligase enzyme component; and
    wherein the set of ligase buffer components are a set of RNA ligase buffer components.

26

4. The device of claim 1,
    where the microfluidics system is a digital microfluidics system.

5. The device of claim 1,
    where the sequence-specific probe is an oligonucleotide strand displacement probe;
    where the at least one polymerase buffer component is a Bst 3.0 polymerase buffer component; and
    where the at least at least one polymerase enzyme with strand displacement activity is a Bst 3.0 polymerase enzyme.

6. The device of claim 5, further comprising:
    a camera system for monitoring fluorescence emanating from the target location and the second target location in response to excitation radiation from a radiation source.

7. The device of claim 1, further comprising:
    a system for cooling a heated fluid at the target location and for cooling a heated fluid at the second target location;
    wherein the heat source is configured to heat fluid located on at least the target location and fluid located on at least the second target location to approximately 95 degrees Celsius; and
    wherein the heat source is further configured to heat fluid located on at least the target location and fluid located on at least the second target location to approximately 65 degrees Celsius.

8. The device of claim 1,
    wherein the movable cartridge assembly is a consumable cartridge.

9. The device of claim 1,
    wherein the at least one target-specific set of reagent components deposited on the surface at the target location are printed at the target location; and
    wherein the second target-specific set of reagent components deposited on the surface at the second target location are printed at the second target location.

10. The device of claim 1,
    wherein the microfluidics system is configured to transport an aliquot of the sample received on the surface to the target location and is further configured to transport a second aliquot of the sample received on the surface to the second target location; and
    wherein the microfluidics system is further configured to transport an aliquot of RCA-LAMP reaction components on the surface to the target location and is further configured to transport a second aliquot of RCA-LAMP reaction components on the surface to the second target location.

11. The device of claim 10,
    wherein the at least one set of RCA-LAMP reaction components deposited on the surface at the RCA-LAMP location are deposited in a dried form; and
    wherein the microfluidics system is further configured to transport an aliquot of hydrated RCA-LAMP reaction components on the surface to the target location and is further configured to transport a second aliquot of hydrated RCA-LAMP reaction components on the surface to the second target location.

12. A method for monitoring fluorescence associated with nucleic acid material in a sample, the method comprising:
    providing a microfluidics system;
        the microfluidics system including a movable cartridge assembly;

the movable cartridge assembly comprising:

a surface configured to receive the sample;

at least one target-specific set of reagent components deposited on the surface at a target location;

at least a second target-specific set of reagent components deposited on the surface at a second target location;

at least one set of RCA-LAMP reaction components deposited on the surface at an RCA-LAMP location;

the at least one target-specific set of reagent components including:

at least one target-specific padlock probe reagent component;

at least one target probe-associated ligase enzyme component; and at least one target probe-associated set of ligase buffer components;

the second target-specific set of reagent components including:

a second target-specific padlock probe reagent component;

the at least one target probe-associated ligase enzyme component; and the at least one target probe-associated set of ligase buffer components; and the at least one set of RCA-LAMP reaction components including:

at least one polymerase buffer component;

at least one polymerase enzyme with strand displacement activity;

a betaine additive;

a poloxamine surfactant additive;

a sequence-specific probe;

dNTPs; and a primer mix;

the primer mix including:

a forward inside primer specific to a backbone of the at least one target-specific padlock probe reagent component; and a backward inside primer specific to the backbone of the at least one target-specific padlock probe reagent component;

wherein the second target-specific padlock probe reagent component includes the backbone of the at least one target-specific padlock probe reagent component;

transporting an aliquot of the sample received on the surface to the target location;

transporting a second aliquot of the sample received on the surface to the second target location;

applying heat to the target location and the second target location;

transporting an aliquot of RCA-LAMP reaction components on the surface to the target location;

transporting a second aliquot of RCA-LAMP reaction components on the surface to the second target location;

applying heat to the target location and the second target location;

providing excitation radiation to the target location and the second target location; and monitoring fluorescence emanating from the target location and the second target location in response to the excitation radiation using a camera system.

13. The method of claim 12, wherein the ligase enzyme component is a Taq DNA ligase enzyme component; and wherein the set of ligase buffer components are a set of Taq DNA ligase buffer components.

14. The method of claim 12, wherein the ligase enzyme component is a RNA ligase enzyme component; and wherein the set of ligase buffer components are a set of RNA ligase buffer components.

15. The method of claim 12, where the microfluidics system is a digital microfluidics system.

16. The method of claim 12, where the sequence-specific probe is an oligonucleotide strand displacement probe;

where the at least one polymerase buffer component is a Bst 3.0 polymerase buffer component; and where the at least at least one polymerase enzyme with strand displacement activity is a Bst 3.0 polymerase enzyme.

17. The method of claim 12, further comprising:

cooling heated fluid at the target location prior to the step of transporting an aliquot of RCA-LAMP reaction components on the surface to the target location; and cooling heated fluid at the second target location prior to the step of transporting a second aliquot of RCA-LAMP reaction components on the surface to the second target location;

wherein the step of applying heat to the target location prior to the step of transporting an aliquot of RCA-LAMP reaction components on the surface to the target location includes heating fluid located on at least the target location to approximately 95 degrees Celsius;

wherein the step of applying heat to the second target location prior to the step of transporting a second aliquot of RCA-LAMP reaction components on the surface to the second target location includes heating fluid located on at least the second target location to approximately 95 degrees Celsius;

wherein the step of applying heat to the target location after the step of transporting an aliquot of RCA-LAMP reaction components on the surface to the target location includes heating fluid located on at least the target location to approximately 65 degrees Celsius; and wherein the step of applying heat to the second target location after the step of transporting a second aliquot of RCA-LAMP reaction components on the surface to the second target location includes heating fluid located on at least the second target location to approximately 65 degrees Celsius.

18. The method of claim 12, wherein the movable cartridge is a consumable cartridge.

19. The method of claim 12, wherein the at least one target-specific set of reagent components deposited on the surface at the target location are printed at the target location; and wherein the second target-specific set of reagent components deposited on the surface at the second target location are printed at the second target location.

20. The method of claim 12, wherein the at least one set of RCA-LAMP reaction components deposited on the surface at the RCA-LAMP location are deposited in a dried form, the method further comprising:

hydrating the RCA-LAMP reaction components;

wherein the step of transporting an aliquot of RCA-LAMP reaction components on the surface to the target location comprises transporting an aliquot of hydrated RCA-LAMP reaction components on the surface to the target location; and wherein the step of transporting a second aliquot of RCA-LAMP reaction components on the surface to the second target location comprises transporting a second aliquot of hydrated RCA-LAMP reaction components on the surface to the second target location.

\* \* \* \* \*